US011400137B2

(12) United States Patent
Olsen et al.

(10) Patent No.: US 11,400,137 B2
(45) Date of Patent: Aug. 2, 2022

(54) RECTAL INSULIN FOR TREATMENT OF INFLAMMATORY BOWEL DISEASES

(71) Applicant: University of Copenhagen, Copenhagen (DK)

(72) Inventors: Jørgen Olsen, Kastrup (DK); Mohammad Taha Yassin, Søborg (DK); Anders Elm Pedersen, Allerød (DK)

(73) Assignee: University of Copenhagen, Copenhagen (DK)

( * ) Notice: Subject to any disclaimer, the term of this patent is extended or adjusted under 35 U.S.C. 154(b) by 234 days.

(21) Appl. No.: 16/348,389

(22) PCT Filed: Nov. 10, 2017

(86) PCT No.: PCT/EP2017/078900
§ 371 (c)(1),
(2) Date: May 8, 2019

(87) PCT Pub. No.: WO2018/087298
PCT Pub. Date: May 17, 2018

(65) Prior Publication Data
US 2021/0038696 A1    Feb. 11, 2021

(30) Foreign Application Priority Data
Nov. 14, 2016  (EP) .................... 16198633

(51) Int. Cl.
*A61K 38/28*   (2006.01)
*A61K 9/00*    (2006.01)
*A61P 35/00*   (2006.01)
*A61K 45/06*   (2006.01)

(52) U.S. Cl.
CPC ............ *A61K 38/28* (2013.01); *A61K 9/0031* (2013.01); *A61P 35/00* (2018.01); *A61K 45/06* (2013.01)

(58) Field of Classification Search
CPC ...... A61K 38/28; A61K 45/06; A61K 9/0031; A61P 1/00; A61P 35/00; Y02A 50/30
See application file for complete search history.

(56) References Cited

U.S. PATENT DOCUMENTS

| 4,338,306 A | 7/1982 | Kitao et al. |
| 4,406,896 A | 9/1983 | Higuchi et al. |
| 2002/0128171 A1* | 9/2002 | Watkins ............... A61K 31/517 514/1 |

FOREIGN PATENT DOCUMENTS

| FR | 2455897 A1 | 12/1980 |
| WO | 9620001 A1 | 7/1996 |
| WO | 9734580 A1 | 9/1997 |
| WO | 2002096392 A1 | 12/2002 |
| WO | 2005007072 A2 | 1/2005 |
| WO | 2005117951 A1 | 12/2005 |
| WO | 2008117125 A2 | 10/2008 |
| WO | 2008132731 A2 | 11/2008 |
| WO | 2008132732 A2 | 11/2008 |
| WO | 2010032140 A2 | 3/2010 |

OTHER PUBLICATIONS

Qiang Sun, New insights into insulin: The anti-inflammatory effect and its clinical relevance, World J Diabetes Apr. 15, 2014; 5(2): 89-96.*
Healthline, https://www.healthline.com/health/inflammatory-bowel-disease#prevention, Inflammatory Bowel Disease (IBD), Acessed on Apr. 19, 2021.*
Atchison, et al., "Colonic absorbtion of insulin: an in vitro and in vivo evaluation", Journal of Pharmacology and Experimental Ther., vol. 248, No. 2, pp. 567-572, (1989).
Olsen, et al., Overexpression of Receptors for Insulin and Epidermal Growth Factor in Dysplastic Inflamed Colonic Mucosa Correlates With Increased Cancer Risk in Patients With Ulcerative Colitis, AGA Abstracts, Sal 932, S-350, (2011).
Katsuma, et al., "Scinitigraphic evaluation of a novel colon target delivery system (CODES) in healthy volunteers", J. Pharm. Sci., vol. 93, No. 5, pp. 1287-1299, (2004).
Räisanen, et al., "Carbonic anhydrase III protects cells from hydrogen peroxide-induced apoptosis", FASEB Journal, vol. 13, No. 3, pp. 513-522, (1999).
Terzic, J. et al., "Inflammation and Colon Cancer", Gasliuenterology, vol. 138, pp. 2101-2114, (2010).
Sadowska, Zuzanna, "Colitis-associated colorectal cancer in mice: in vivo disease imaging and insight into the AOM/DSS model", Pure and Applied Biochemistry, (2016), (Abstract).
Wehkamp, et al., "Inflammatory Bowel Disease", Crohn's disease and ulcerative colitis., Dtsch Arztebl Int., vol. 113, No. 5, pp. 72-82, (2016).
Woods, et al., "Wireless Capsule Endoscope for Targeted Drug Delivery: Mechanics and Design Consideration", IEEE transactions on biomedical engineering, vol. 60, No. 4, pp. 945-953, (2013).
Database WPI; Week 199120; Thomson Scientific, London, GB; AN 1991-146147; (Apr. 1991).

\* cited by examiner

*Primary Examiner* — Julie Ha
*Assistant Examiner* — Erinne R Dabkowski
(74) *Attorney, Agent, or Firm* — Ice Miller LLP

(57) ABSTRACT

The present disclosure relates to compositions comprising insulin and to be administered rectally for treatment of inflammatory bowel diseases and inflammation-induced colorectal tumour and/or cancer.

21 Claims, 13 Drawing Sheets

RECTAL INSULIN FOR TREATMENT OF INFLAMMATORY BOWEL DISEASES

CROSS-REFERENCE TO RELATED APPLICATION

This application is a Section 371 of International Application No. PCT/EP2017/078900, filed Nov. 10, 2017, which was published in the English language on May 17, 2018, under International Publication No. WO 2018/087298 A1, which claims priority under 35 U.S.C. § 119(b) to European Patent Application No. 16198633.6, filed on Nov. 14, 2016, the disclosures of which are incorporated herein by reference in their entireties.

TECHNICAL FIELD

The present invention relates to compositions comprising insulin and to be administered rectally for treatment of inflammatory bowel diseases and inflammation-induced colorectal tumour and/or cancer.

BACKGROUND

Inflammatory bowel diseases (IBDs) are common in Europe, with prevalence as high as 1 in 198 persons (ulcerative colitis) and 1 in 310 persons (Crohn's disease) (Wehkamp J et al. 2016). Both young and elderly are affected and once diagnosed IBD is a chronic condition characterized by alternating episodes of inflammation with acute symptoms and remission which is asymptomatic. In the long term perspective especially ulcerative colitis (UC) is a known risk factor for development of colorectal tumours and cancer.

Crohn's disease and ulcerative colitis, two varieties of inflammatory bowel disease (IBD), both tend to arise in early adulthood, but can in fact arise at any age from early childhood onward. Their diagnosis is often delayed despite their prominent manifestations, including diarrhoea, abdominal pain, and, in ulcerative colitis, peranal bleeding. Crohn's disease can affect the entire gastrointestinal tract transmurally, from the mouth to the anus, while ulcerative colitis mainly affects the colonic mucosa. The clinical picture is rounded out by extra-intestinal manifestations in the joints, eyes, and skin, which can arise before the bowel disease does.

IBD patients, unlike healthy individuals, have bacteria directly on and in their mucosal epithelium.

IBDs are now thought of as complex barrier disorders. The mucosal barrier consists of the epithelial layer and the antibacterial mucus layer above it, which is made up of goblet cell mucins and epithelially secreted intrinsic peptide antibiotics (defensins). In ulcerative colitis, a defective, thinned mucus layer is seen. In Crohn's disease of the small intestine, the Paneth cells at the base of the crypts and defective defensin formation seem to play a central role. Various defects of bacterial recognition (NOD2), autophagy, endoplasmic reticulum stress, and monocyte function impair antimicrobial defences and alter the microbiome. Invading bacteria induce an inflammatory response involving both the innate immune cells (granulocytes, macrophages, dendritic cells) and the adaptive immune cells (T cells).

The natural course of IBD is highly variable: a patient may experience a mild course after a severe initial episode, a slowly or episodically progressive condition, or chronically intermittent or persistent symptoms. After an initial acute episode, there is a 40% chance of a remitting course, also called re-occurrence or relapse, with prolonged phases of disease inactivity, also called remission phases, between episodes. About 20% of all patients develop steroid-refractory disease; the remainder are steroid-dependent, i.e., they rapidly develop recurrent disease when any attempt is made to lower the steroid dose.

The most common early symptoms of IBD are chronic diarrhoea (which is sometimes bloody), cramping abdominal pain, fever, loss of appetite, and weight loss. Symptoms may continue for days or weeks and may resolve without treatment. IBD relapses at irregular intervals throughout the lifespan of a subject. Relapse can be mild, moderate or severe, brief or prolonged. Severe relapses can lead to intense pain, dehydration, and blood loss. A subject is in remission when none of the above symptoms is present.

Inflammation-induced colorectal tumour and, also called colitis-associated cancer (CAC), is the subtype of colorectal cancer that is associated with IBDs, is difficult to treat, and has high mortality. More than 20% of IBD patients develop inflammation-induced colorectal cancer within 30 years of disease onset, and 50% of these will die from it (Terzic et al. 2010).

Several of the currently used treatments for inflammatory bowel diseases, in particular for Crohn's disease and ulcerative colitis, have severe side effects and their use should thus be as short as possible. In addition, some individuals are resistant to some of the currently used drugs. Indeed up to 50% of the IBD patients do not respond satisfactorily to the most frequently used drug (5-aminosalicylate) and up to 20% of the IBD patients do not respond to the second most used drug (corticosteroids).

Alternative therapies suitable for a large portion of the individuals affected by IBD with reduced side effects are needed. Additionally, treatments reducing the risk for development of colorectal cancer in IBD subjects are desirable.

SUMMARY

The present disclosure relates to the finding that rectal administration of insulin to an individual suffering from or suspected of suffering from an inflammatory bowel disease results in mucosa healing during inflammation, induces and also maintains remission. Furthermore, rectal administration of insulin to an individual suffering from or suspected of suffering from an inflammatory bowel disease also results in reduced occurrence of inflammation-induced colorectal tumour and/or cancers.

One of the advantages of the present invention is that rectally administered insulin has low or no systemic effects and therefore minimal or no side effects.

In a first aspect, the present disclosure relates to a composition comprising a therapeutically effective amount of insulin or a pharmaceutically acceptable salt thereof for use in a method of treatment of inflammatory bowel disease and/or inflammation-induced colorectal tumour and/or cancer, wherein the composition is administered rectally to a subject in need thereof.

In another aspect, the present disclosure relates to a method for treatment of an inflammatory bowel disease and/or inflammation-induced colorectal tumour and/or cancer in a subject in need thereof, the method comprising rectal administration of a composition comprising a therapeutically effective amount of insulin or a pharmaceutically acceptable salt thereof.

In a further aspect, the present disclosure relates to a method of reducing weight loss in a subject suffering from or suspected of suffering from an inflammatory bowel disease and/or inflammation-induced colorectal tumour and/or cancer, the method comprising rectal administration of a composition comprising a therapeutically effective amount of insulin or a pharmaceutically acceptable salt thereof.

In an even further aspect, the present disclosure relates to a method of healing colonic mucosa in a subject suffering from or suspected of suffering from an inflammatory bowel disease and/or inflammation-induced colorectal tumour and/or cancer, the method comprising rectal administration of a composition comprising a therapeutically effective amount of insulin or a pharmaceutically acceptable salt thereof.

DEFINITIONS

Figure 1:
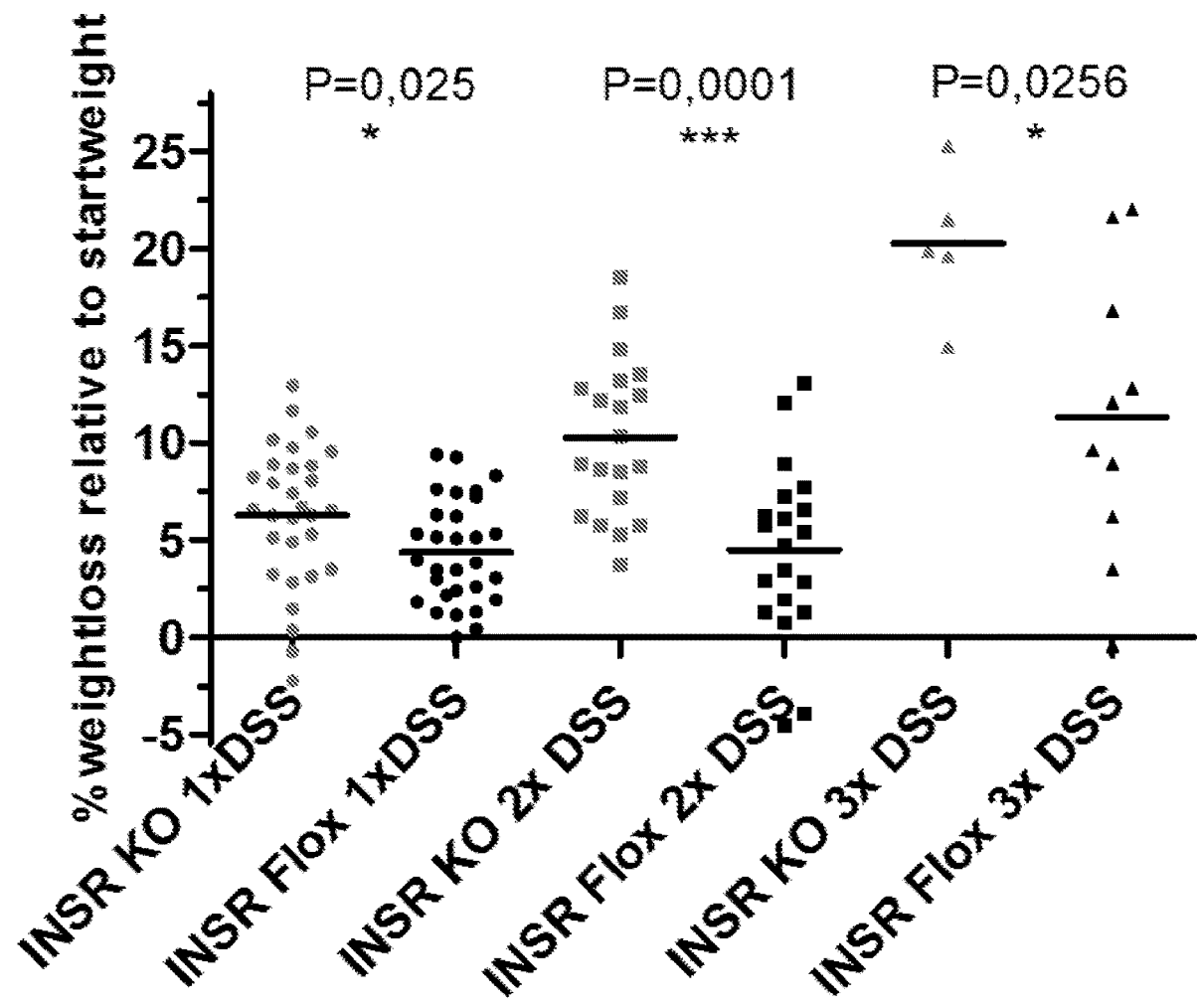
FIG. 1. Insulin signalling inhibits DSS colitis. Mice with intestinal specific inactivation of the insulin receptor (INSR KO) develop more severe colonic inflammation, as indicated by the higher weight loss, than control mice (INSR Flox).

The terms "treatment" and "treating" as used herein refer to the management and care of a patient for the purpose of combating a condition, disease or disorder. The term is intended to include the full spectrum of treatments for a given condition from which the patient is suffering or is suspected of suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering, reducing or delaying the development of the condition, disease or disorder, and includes the administration of the active compounds to prevent or reduce the risk of the onset of symptoms or complications. The treatment may thus be a prophylactic treatment. The patient to be treated is preferably a mammalian, in particular a human being. The patients to be treated can be of various ages.

An "Inflammatory bowel disease" or "IBD" is a group of inflammatory conditions of the colon and small intestine. The major types of IBD are Crohn's disease and ulcerative colitis (UC). Accounting for far fewer cases are other forms of IBD:

Collagenous colitis
Lymphocytic colitis
Ischaemic colitis
Diversion colitis
Behçet's disease
Indeterminate colitis
left sided colitis,
noninfective colitis.

A "subject" is an individual of one of the species of mammals or poultry disclosed herein. A "patient" is a subject, which is suffering from, suspected of suffering from or who has been diagnosed with a particular disorder.

The "large intestine" or "large bowel" is the last part of the gastrointestinal tract of the digestive system in vertebrates. It comprises cecum, colon, rectum, and anal canal. In humans, the large intestine begins in the right iliac region of the pelvis, just at or below the waist, where it is joined to the end of the small intestine at the cecum, via the ileocecal valve. It then continues as the colon ascending the abdomen, across the width of the abdominal cavity as the transverse colon, and then descending to the rectum and its endpoint at the anal canal. Overall, in humans, the large intestine is about 1.5 metres long, which is about one-fifth of the whole length of the gastrointestinal tract.

The term "remission" denotes herein periods with disease control, i.e. periods where symptoms are essentially absent, versus active disease, wherein symptoms are present, which are often referred to as "attack" or "acute phase". For example, the term remission used in the context of IBDs refers to absence of active cancer or inflammatory bowel disease when these diseases are expected to manifest again in the future. A subject in remission usually follows a maintenance therapy. The most common early symptoms of IBD are chronic diarrhea (which is sometimes bloody), cramping abdominal pain, fever, loss of appetite, and weight loss. Other symptoms are abdominal pain, vomiting, rectal bleeding, severe internal cramps/muscle spasms in the region of the pelvis, deep geographic and serpiginous ulcers, continuous ulcer, transmural inflammation, mucosal inflammation, stenosis, granulomas on biopsy (for example non-necrotizing non-peri-intestinal crypt granulomas), high levels of faecal calprotectin, anaemia, thrombocytosis, architectonic abnormalities of the rectal tissue on histological examination, fistulae or abscesses to any segment of the gastrointestinal tract, toxic megacolon. During the remission phase, the above listed symptoms are not present. This phase can thus also be termed asymptomatic.

The "acute phase" or "attack" is a period of active disease wherein the activity of the disease may be of various intensities, usually classified as mild, moderate or severe, which correspond to very low, low and high intensity, respectively. A subject suffering or suspected of suffering from an attack or a relapse usually follows an induction therapy, which is a therapy that induces remission. A disease may also be very severe, so-called "fulminant". A fulminant IBD usually requires immediate surgical intervention, but the composition of the present disclosure may be used as a supplementary therapy prior, simultaneously with or after surgery.

The term "relapse" denotes herein re-occurrence of the symptoms of IBD. The most common early symptoms of IBD are chronic diarrhoea (which is sometimes bloody), cramping abdominal pain, fever, loss of appetite, and weight loss. Other symptoms are listed above. Symptoms may continue for days or weeks and may resolve without treatment. IBD relapses at irregular intervals throughout the lifespan of a subject. Relapse can be mild or severe, brief or prolonged. Severe relapses can lead to intense pain, dehydration, and blood loss.

"Inflammation-induced colorectal tumour and/or cancer" is a form of colorectal tumour and/or cancer that develops in subjects suffering from or suspected of suffering from IBDs. Inflammation-induced colorectal tumour and/or cancer appears to have a different aetiology, carcinogenesis pathway and clinical course than its sporadic counterpart. Therefore, different treatment approaches may be necessary.

A "unit" or "unit of insulin" or "U" or "IU" as used herein is defined as the biological equivalent of 34.7 µg pure crystalline insulin, which also corresponds to 6 µmol (provided that the molecular mass of insulin is considered to be 5800 Da. This corresponds to the old United States Pharmacopeia insulin unit, where one unit (U) of insulin was set equal to the amount required to reduce the concentration of blood glucose in a fasting rabbit to 45 mg/dl (2.5 mmol/L).

"Local administration" is used in the present disclosure to indicate that the compositions are delivered to a certain "localized" area of the body of a subject in need thereof and act locally at the site of administration. In particular, the present disclosure is directed to "rectal administration" of insulin, which corresponds to administration of insulin to the rectum, or more in general to the large intestine, of a subject in need thereof and wherein said insulin acts almost exclusively on the cells of the large intestine. Accordingly, a rectally administered pharmaceutically active ingredient is not adsorbed by the intestine and thus it is not taken up into the blood stream of the treated subject.

DETAILED DESCRIPTION

The present disclosure relates to rectal administration of insulin for treatment of an inflammatory bowel disease and/or inflammation-induced colorectal tumour and/or cancer in an individual in need thereof.

Inflammatory Bowel Diseases

Crohn's disease and ulcerative colitis, two varieties of inflammatory bowel disease (IBD), both tend to arise in early adulthood, but can in fact arise at any age from early childhood onward. Their diagnosis is often delayed despite their prominent manifestations, including diarrhoea, abdominal pain, and, in ulcerative colitis, peranal bleeding. Crohn's disease can affect the entire gastrointestinal tract transmurally, from the mouth to the anus, while ulcerative colitis mainly affects the colonic mucosa. The clinical picture is rounded out by extra-intestinal manifestations in the joints, eyes, and skin, which can arise before the bowel disease does.

IBD patients, unlike healthy individuals, have bacteria directly on and in their mucosal epithelium.

IBDs are now thought of as complex barrier disorders. The mucosal barrier consists of the epithelial layer and the antibacterial mucus layer above it, which is made up of goblet cell mucins and epithelially secreted intrinsic peptide antibiotics (defensins). In ulcerative colitis, a defective, thinned mucus layer is seen. In Crohn's disease of the small intestine, the Paneth cells at the base of the crypts and defective defensin formation seem to play a central role. Various defects of bacterial recognition (NOD2), autophagy, endoplasmic reticulum stress, and monocyte function impair antimicrobial defences and alter the microbiome. Invading bacteria induce an inflammatory response involving both the innate immune cells (granulocytes, macrophages, dendritic cells) and the adaptive immune cells (T cells).

The natural course of IBD is highly variable: a patient may experience a mild course after a severe initial episode, a slowly or episodically progressive condition, or chronically intermittent or persistent symptoms. After an initial acute episode, there is a 40% chance of a remitting course, also called re-occurrence or relapse, with prolonged phases of disease inactivity, also called remission phases, between episodes. About 20% of all patients develop steroid-refractory disease; the remainder are steroid-dependent, i.e., they rapidly develop recurrent disease when any attempt is made to lower the steroid dose.

A subject suffering from or suspected of suffering from an IBD usually presents periods of disease, when the symptoms of the IBD are present, and periods of remission, when no symptoms are present. After a period of remission, the symptoms may return and there can be re-occurrence or relapse.

The most common early symptoms of IBD are chronic diarrhoea (which is sometimes bloody), cramping abdominal pain, fever, loss of appetite, and weight loss. Symptoms may continue for days or weeks and may resolve without treatment. IBD relapses at irregular intervals throughout the lifespan of a subject. Relapse can be mild, moderate or severe, brief or prolonged. Severe relapses can lead to intense pain, dehydration, and blood loss. A subject is in remission when none of the above symptoms is present.

The present disclosure relates to compositions comprising a therapeutically effective amount of insulin or a pharmaceutically acceptable salt thereof for use in a method of treatment of inflammatory bowel disease, wherein the composition is administered rectally to a subject in need thereof. In some embodiments of the present disclosure, the inflammatory bowel disease is selected from the group consisting of ulcerative colitis, microscopic colitis such as collagenous colitis or lymphocytic colitis, diversion colitis, Behçet's disease, indeterminate colitis, left sided colitis, noninfective colitis, Crohn's disease and pouchitis.

In some embodiments of the present disclosure, the inflammatory bowel disease is selected from the group consisting of ulcerative colitis, diversion colitis, Behçet's disease, indeterminate colitis, left sided colitis, noninfective colitis, Crohn's disease and pouchitis.

In some embodiments of the present disclosure, the inflammatory bowel disease is ulcerative colitis.

In some embodiments of the present disclosure, the inflammatory bowel disease is Crohn's disease.

In some embodiments of the present disclosure, the inflammatory bowel disease is diversion colitis.

In some embodiments of the present disclosure, the inflammatory bowel disease is Behçet's disease.

In some embodiments of the present disclosure, the inflammatory bowel disease is indeterminate colitis.

In some embodiments of the present disclosure, the inflammatory bowel disease is left sided colitis.

In some embodiments of the present disclosure, the inflammatory bowel disease is noninfective colitis.

In some embodiments of the present disclosure, the inflammatory bowel disease is pouchitis.

In some embodiments of the present disclosure, the inflammatory bowel disease is not infectious colitis.

Pouchitis is the inflammation of the ileal pouch (an artificial rectum surgically created out of ileal gut tissue in patients who have undergone a colectomy), which is created in the management of patients with ulcerative colitis, indeterminate colitis, familial adenomatous polyposis (FAP), or, in some cases other colitis. Subjects with pouchitis typically present symptoms associated with IBDs, in particular bloody diarrhoea, extreme cramping and abdominal pain.

Ulcerative colitis is normally continuous from the rectum up the colon. The disease is classified by the extent of involvement, depending on how far up the colon the disease extends, into (a) distal colitis, which includes proctitis, proctosigmoiditis and left-sided colitis, and (b) extensive colitis, which includes pancolitis. For the purpose of this disclosure, the term "ulcerative colitis" refers to any one of the forms in which the disease presents itself, in particular the above mentioned forms.

Diagnosis of an IBD is usually considered to be complex; several analyses and/or examinations may be required and therefore the diagnosis may come long time after a subject has sought medical advice.

The composition comprising insulin for rectal administration as disclosed herein may be administered to a subject in need thereof who presents one or more symptoms typical of IBDs and/or inflammation-induced colorectal tumour and/or cancer, but who has not yet being diagnosed as suffering from said diseases.

In some embodiments of the present disclosure, the composition is administered to a subject in need thereof, wherein the subject presents one or more of the following symptoms: abdominal pain, vomiting, chronic diarrhoea, rectal bleeding, severe internal cramps/muscle spasms in the region of the pelvis, weight loss, deep geographic and serpiginous ulcers, continuous ulcer, transmural inflammation, mucosal inflammation, stenosis, granulomas on biopsy (for example non-necrotizing non-peri-intestinal crypt granulomas), high levels of faecal calprotectin, anaemia, thrombocytosis, architectonic abnormalities of the rectal tissue on histological examination, fistulae or abscesses to any segment of the gastrointestinal tract, toxic megacolon.

In some embodiments of the present disclosure, the composition is administered to a subject who has been diagnosed with an inflammatory bowel disease and/or inflammation-induced colorectal tumour and/or cancer.

One aspect of the present disclosure relates to a method for treatment of an inflammatory bowel disease in a subject in need thereof, the method comprising rectal administration of a composition comprising a therapeutically effective amount of insulin or a pharmaceutically acceptable salt thereof as disclosed herein.

Another aspect of the present disclosure relates to a method of reducing weight loss in a subject suffering from or suspected of suffering from an inflammatory bowel disease, the method comprising rectal administration of a composition comprising a therapeutically effective amount of insulin or a pharmaceutically acceptable salt thereof as disclosed herein.

A further aspect of the present disclosure relates to a method of healing colonic mucosa in a subject suffering from or suspected of suffering from an inflammatory bowel disease, the method comprising rectal administration of a composition comprising a therapeutically effective amount of insulin or a pharmaceutically acceptable salt thereof as disclosed herein.

Rectal administration of insulin or a pharmaceutically acceptable salt thereof as disclosed herein to a subject suffering from or suspected of suffering from an IBD results in a reduction of weight loss of said subject, for example the subject may lose less weight, maintain his or her weight or even gain weight in comparison to subjects suffering from or suspected of suffering from an IBD and not receiving the insulin composition.

Rectal administration of insulin or a pharmaceutically acceptable salt thereof to a subject suffering from or suspected of suffering from an IBD results in other effects, for example rectal bleeding is reduced as well as number, size and severity of colorectal tumours associated with inflammation. A subject suffering from or suspected of suffering from an IBD presents a reduction of the symptoms typical for IBDs, which are described elsewhere in this disclosure, as a result of the rectal administration of a composition comprising insulin.

The composition comprising insulin as disclosed herein can be used as monotherapy for treatment of an IBD both as an induction therapy, for example during an attack or in case of relapse, and as a maintenance therapy, for example during the remission phase of the disease. Alternatively, the composition comprising insulin as disclosed herein can be used in combination with other therapies for treatment of an IBD both as an induction therapy and as a maintenance therapy.

In some embodiments of the present disclosure, the composition comprising insulin is administered to a subject suffering from or suspected of suffering from an inflammatory bowel disease during the acute phase and/or during relapse of the disease.

In some embodiments of the present disclosure, the composition is administered to a subject suffering from or suspected of suffering from an inflammatory bowel disease during the remission phase of the disease.

In some embodiments of the present disclosure, the composition is administered to a subject suffering from or suspected of suffering from mild to moderate ulcerative colitis.

In some embodiments of the present disclosure, the composition is administered to a subject suffering from or suspected of suffering from mild to moderate ulcerative colitis during the acute phase and/or during relapse of the disease.

In some embodiments of the present disclosure, the composition is administered to a subject suffering from or suspected of suffering from mild to moderate ulcerative colitis during the remission phase of the disease.

In some embodiments of the present disclosure, the composition is administered to a subject suffering from or suspected of suffering from Crohn's disease.

In some embodiments of the present disclosure, the composition is administered to a subject suffering from or suspected of suffering from Crohn's disease during the acute phase and/or during relapse of the disease.

In some embodiments of the present disclosure, the composition is administered to a subject suffering from or suspected of suffering Crohn's disease during the remission phase of the disease.

Inflammation-Induced Colorectal Tumour and/or Cancers

Inflammation-induced colorectal tumour, also called colitis-associated cancer (CAC), is the subtype of colorectal cancer that is associated with IBDs, is difficult to treat, and has high mortality. More than 20% of IBD patients develop inflammation-induced colorectal cancer within 30 years of disease onset, and 50% of these will die from it (Terzic et al. 2010).

Chronic inflammation precedes inflammation-induced tumour development. Chronic inflammation causes oxidative damage to DNA, leading to the p53 mutations observed in tumour cells and the inflamed, but nondysplastic epithelium. Inflammation-induced mutagenesis can also cause inactivation or repression of MMR genes and ROS can directly oxidize and inactivate mismatch repair enzymes at protein level (Terzic et al. 2010).

The present compositions are useful for treatment of inflammation-induced colorectal tumour and/or cancers.

One aspect of the present disclosure relates to a method for treatment of inflammation-induced colorectal tumour and/or cancer in a subject in need thereof, the method comprising rectal administration of a composition comprising a therapeutically effective amount of insulin or a pharmaceutically acceptable salt thereof as disclosed herein.

Another aspect of the present disclosure relates to a method of reducing weight loss in a subject suffering from or suspected of suffering from inflammation-induced colorectal tumour and/or cancer, the method comprising rectal administration of a composition comprising a therapeutically effective amount of insulin or a pharmaceutically acceptable salt thereof as disclosed herein.

A further aspect of the present disclosure relates to a method of healing colonic mucosa in a subject suffering from or suspected of suffering from inflammation-induced colorectal tumour and/or cancer, the method comprising rectal administration of a composition comprising a therapeutically effective amount of insulin or a pharmaceutically acceptable salt thereof as disclosed herein.

Inflammation-induced colorectal tumour or cancer is a neoplasm of the large intestine, for example a malignant neoplasm of the large intestine. The neoplasm may be located in any one of caecum, appendix, ascending colon, transverse colon, descending colon, sigmoid colon, hepatic flexure, splenic flexure, rectosigmoid junction, rectum, anus, anal canal and cloacogenic zone. The location of the neoplasm may also overlap on two or more of the above mentioned areas of the large intestine.

Rectal administration of insulin or a pharmaceutically acceptable salt thereof as disclosed herein to a subject suffering from or suspected of suffering from inflammation-induced colorectal tumour and/or cancer results in a reduction of weight loss of said subject, for example the subject may lose less weight, maintain his or her weight or even gain weight in comparison to subjects suffering from or suspected of suffering from inflammation-induced colorectal tumour and not receiving the insulin composition.

A subject suffering from or suspected of suffering from inflammation-induced colorectal tumour and/or cancer presents a reduction of the symptoms typical for IBDs, which are described elsewhere in this disclosure, as a result of the rectal administration of a composition comprising insulin.

The composition comprising insulin as disclosed herein can be used as monotherapy for treatment of inflammation-induced colorectal tumour and/or cancer both as an induction therapy, for example during an attack or in case of relapse, and as a maintenance therapy, for example during the remission phase of the disease. Alternatively, the composition comprising insulin as disclosed herein can be used in combination with other therapies for treatment of inflammation-induced colorectal tumour and/or cancer both as an induction therapy and as a maintenance therapy.

In some embodiments of the present disclosure, the composition comprising insulin is administered to a subject suffering from or suspected of suffering from inflammation-induced colorectal tumour and/or cancer during the acute phase and/or during relapse of the disease.

In some embodiments of the present disclosure, the composition is administered to a subject suffering from or suspected of suffering from inflammation-induced colorectal tumour and/or cancer during the remission phase of the disease.

Composition Comprising Insulin for Treatment of IBDs and Inflammation-Induced Colorectal Tumour and/or Cancers The present disclosure relates to treatment of IBDs and/or inflammation-induced colorectal tumour and/or cancer via rectal administration of insulin.

One aspect of the present disclosure relates to a composition comprising a therapeutically effective amount of insulin or a pharmaceutically acceptable salt thereof for use in a method of treatment of inflammatory bowel disease and/or inflammation-induced colorectal tumour and/or cancer, wherein the composition is administered rectally to a subject in need thereof.

Another aspect of the present disclosure relates to a method for treatment of an inflammatory bowel disease and/or inflammation-induced colorectal tumour and/or cancer in a subject in need thereof, the method comprising rectal administration of a composition comprising a therapeutically effective amount of insulin or a pharmaceutically acceptable salt thereof as disclosed herein.

A further aspect of the present disclosure relates to a method of reducing weight loss in a subject suffering from or suspected of suffering from an inflammatory bowel disease and/or inflammation-induced colorectal tumour and/or cancer, the method comprising rectal administration of a composition comprising a therapeutically effective amount of insulin or a pharmaceutically acceptable salt thereof as disclosed herein.

An even further aspect of the present disclosure relates to a method of healing colonic mucosa in a subject suffering from or suspected of suffering from an inflammatory bowel disease and/or inflammation-induced colorectal tumour and/or cancer, the method comprising rectal administration of a composition comprising a therapeutically effective amount of insulin or a pharmaceutically acceptable salt thereof as disclosed herein.

The methods of the present disclosure as described in detail in the above sections "Inflammatory bowel disease" and "Inflammation-induced colorectal tumour and/or cancer". These methods have in common administration of a composition comprising insulin, wherein the insulin is delivered to the large intestine.

In particular, the present disclosure is directed to "rectal administration" of insulin, which corresponds to administration of insulin to the rectum, or more in general to the large intestine, of a subject in need thereof and wherein said insulin acts almost exclusively on the cells of the large intestine. Accordingly, a rectally administered pharmaceutically active ingredient is not adsorbed by the intestine and thus it is not taken up into the blood stream of the treated subject. According to the present disclosure, insulin may be ingested orally and be released in the large intestine, as is known in the art for other compounds. Woods et al., 2015, describe wireless capsule endoscope for targeted drug delivery to various areas of the intestine. Katsuma et al., 2004, describe a colon-targeted delivery system (CODES) administered to healthy volunteers using gamma scintigraphy Rectal administration of insulin or a pharmaceutically acceptable salt thereof according to the present disclosure is generally intended for use in the treatment of chronic colonic inflammation in subject presenting ulcerations in the colonic mucosa, for example colonic mucosa presenting denuded epithelial areas, and/or defects of the colonic epithelial barrier due to alterations in the expression of membrane transporters and/or of proteins involved in cellular polarity.

In some embodiments of the present disclosure, the composition is administered to a subject suffering from or suspected of suffering from an inflammatory bowel disease.

In some embodiments of the present disclosure, the disclosed composition reduces inflammation of epithelial cells of the colon.

For example, reduction of inflammation can be measured by the reduction of expression of Cyclooxygenase 2 (COX2/PTGS2), which is usually higher in colonic epithelial cells of subjects suffering or suspected of suffering from colonic inflammation, such as colonic Crohn's disease or ulcerative colitis, compared to colonic epithelial cells of subjects not suffering from colonic inflammation. Reduction of inflammation can also be measured by monitoring the expression of other inflammation markers.

In some embodiments of the present disclosure, the disclosed composition reduces expression of COX2 mRNA in colonic epithelial cells.

In some embodiments of the present disclosure, the disclosed composition increases the expression of Carbonic anhydrase 3 (Car3) mRNA in colonic epithelial cells.

Car3 encodes a cytosolic carbonic anhydrase and in the colonic epithelial cells carbonic anhydrases is involved in the electroneutral NaCl transport across the epithelium. Car3 also has a role as a scavenger of reactive oxygen species (ROS) (Raisanen et al. 1999, Carbonic anhydrase III protects cells from hydrogen peroxide-induced apoptosis, FASEB Journal 13(3):513-22).

In some embodiments of the present disclosure, the disclosed composition improves epithelial ion transport in the large intestine by regulating the expression of genes involved in transmembrane ion transport, for example by increasing the expression of Car3 mRNA.

In some embodiments of the present disclosure, the disclosed composition improves protection of epithelial cells of the large intestine from reactive oxygen species (ROS) released by the inflamed cells.

In some embodiments of the present disclosure, rectally administered insulin does not cause cell proliferation in the small intestine.

One aspect of the present disclosure relates to a composition comprising a therapeutically effective amount of insulin or a pharmaceutically acceptable salt thereof for use in a method of treatment of inflammatory bowel disease and/or inflammation-induced colorectal tumour and/or cancer, wherein the composition is administered rectally to a subject in need thereof and wherein the composition increases the expression of Car3 mRNA in epithelial cells of the large intestine.

A further aspect of the present disclosure relates to a method of treatment of inflammatory bowel disease and/or inflammation-induced colorectal tumour and/or cancer by increasing the expression of Car3 mRNA epithelial cells of the large intestine.

An even further aspect of the present disclosure relates to a composition comprising a therapeutically effective amount of insulin or a pharmaceutically acceptable salt thereof for increasing the expression of Car3 mRNA epithelial cells of the large intestine.

Dosage

In some embodiments of the present disclosure the composition comprises between 0.01 U and 1000 U of insulin. Rectally administered insulin does not usually have systemic effects on the subject, therefore a high dosage can be administered with low or no side effects.

In some embodiments of the present disclosure rectally administered insulin does not have systemic effects, such as it does not affect systemic blood glucose levels.

Moreover, because no systemic effects are intended, the amount of insulin administered is not dependent on the body weight of the subject, but on the severity of the inflammation. The rectally administered insulin will in fact exercise its therapeutic effect mostly in the large intestine. The dosage will for example be low for a subject in remission phase, suffering or suspected of suffering from a mild IBD. In contrast, a high dosage might be required for treatment of a subject suffering or suspected of suffering from a moderate or severe IBD.

Other factors may affect the dosage. For example, whether other supplementary treatments are administered simultaneously to the insulin, see the section "Further treatment" below.

In some embodiments of the present disclosure the composition comprises between 0.01 IU and 900 IU, such as between 0.01 IU and 800 IU, such as between 0.01 IU and 800 IU, such as between 0.01 IU and 700 IU, such as between 0.01 IU and 600 IU, such as between 0.01 IU and 500 IU, such as between 0.01 IU and 400 IU, such as between 0.01 IU and 300 IU, such as between 0.01 IU and 200 IU, such as between 0.01 IU and 100 IU, such as between 0.01 IU and 50 IU, such as between 0.01 IU and 25 IU, such as between 0.01 IU and 10 IU, such as between 0.01 IU and 1 IU, such as between 0.01 IU and 0.1 IU.

In some embodiments of the present disclosure the composition comprises between 0.01 IU and 1000 IU, such as between 1 IU and 1000 IU, such as between 10 IU and 1000 IU, such as 25 IU and 1000 IU, such as between 50 IU and 1000 IU, such as between 100 IU and 1000 IU, such as between 200 IU and 1000 IU, such as between 300 IU and 1000 IU, such as between 400 IU and 1000 IU, such as between 500 IU and 1000 IU, such as between 600 IU and 1000 IU, such as between 700 IU and 1000 IU, such as between 800 IU and 1000 IU.

In some embodiments of the present disclosure the composition comprises between 0.35 µg and 35 g of insulin, such as between 0.35 µg and 30 g of insulin, such as between 0.35 µg and 25 g of insulin, such as between 0.35 µg and 20 g of insulin, such as between 0.35 µg and 15 g of insulin, such as between 0.35 µg and 10 g of insulin, such as between 0.35 µg and 5 g of insulin, such as between 0.35 µg and 1 g of insulin, such as between 0.35 µg and 100 mg of insulin, such as between 0.35 µg and 50 mg of insulin, such as between 0.35 µg and 1 mg of insulin, such as between 0.35 µg and 100 µg of insulin, such as between 0.35 µg and 50 µg of insulin, such as between 0.35 µg and 10 µg of insulin, such as between 0.35 µg and 1 µg of insulin.

In some embodiments of the present disclosure the composition comprises between 0.35 µg and 35 g of insulin, such as between 1 µg and 35 g of insulin, such as between 10 µg and 35 g of insulin, such as between 50 µg and 35 g of insulin, such as between 100 µg and 35 g of insulin, such as between 1 mg and 35 g of insulin, such as between 10 mg and 35 g of insulin, such as between 50 mg and 35 g of insulin, such as between 100 mg and 35 g of insulin, such as between 1 g and 35 g of insulin, such as between 10 g and 35 g of insulin, such as between 20 g and 35 g of insulin.

In some embodiments of the present disclosure the composition comprises between 0.006 µmol and 6 mol of insulin, such as between 0.006 µmol and 1 mol of insulin, such as between 0.006 µmol and 100 mmol of insulin, such as between 0.006 µmol and 50 mmol of insulin, such as between 0.006 µmol and 10 mmol of insulin, such as between 0.006 µmol and 1 mmol of insulin, such as between 0.006 µmol and 100 µmol of insulin, such as between 0.006 µmol and 50 µmol of insulin, such as between 0.006 µmol and 10 µmol of insulin, such as between 0.006 µmol and 1 µmol of insulin, such as between 0.006 µmol and 0.1 µmol of insulin, such as between 0.006 µmol and 0.01 µmol of insulin.

In some embodiments of the present disclosure the composition comprises between 0.006 µmol and 6 mol of insulin, such as between 0.01 µmol and 6 mol of insulin, such as between 0.05 µmol and 6 mol of insulin, such as between 0.1 µmol and 6 mol of insulin, such as between 0.5 µmol and 6 mol of insulin, such as between 1 µmol and 6 mol of insulin, such as between 10 µmol and 6 mol of insulin, such as between 50 µmol and 6 mol of insulin, such as between 100 µmol and 6 mol of insulin, such as between 1 mmol and 6 mol of insulin, such as between 10 mmol and 6 mol of insulin, such as between 50 mmol and 6 mol of insulin, such as between 100 mmol and 6 mol of insulin, such as between 1 mol and 6 mol of insulin, such as between 2 mol and 6 mol of insulin, such as between 3 mol and 6 mol of insulin, such as between 4 mol and 6 mol of insulin, such as between 5 mol and 6 mol of insulin.

In some embodiments of the present disclosure the composition comprises between 0.01 IU/ml and 10 IU/ml, such as between 0.01 IU/ml and 9 IU/ml, such as between 0.01 IU/ml and 8 IU/ml, such as between 0.01 IU/ml and 7 IU/ml, such as between 0.01 IU/ml and 6 IU/ml, such as between 0.01 IU/ml and 5 IU/ml, such as between 0.01 IU/ml and 4 IU/ml, such as between 0.01 IU/ml and 3 IU/ml, such as between 0.01 IU/ml and 2 IU/ml, such as between 0.01 IU/ml and 1 IU/ml, such as between 0.01 IU/ml and 0.1 IU/ml, such as between 0.1 IU/ml and 10 IU/ml, such as between 1 IU/ml and 10 IU/ml, such as between 2 IU/ml and 10 IU/ml, such as between 3 IU/ml and 10 IU/ml, such as between 4 IU/ml and 10 IU/ml, such as between 5 IU/ml and 10 IU/ml, such as between 6 IU/ml and 10 IU/ml, such as between 7 IU/ml and 10 IU/ml, such as between 8 IU/ml and 10 IU/ml, such as between 9 IU/ml and 10 IU/ml.

In some embodiments of the present disclosure the composition comprises between 0.35 µg/ml and 350 µg/ml of insulin, such as between 0.35 µg/ml and 300 µg/ml of insulin, such as between 0.35 µg/ml and 250 µg/ml of insulin, such as between 0.35 µg/ml and 200 µg/ml of insulin, such as between 0.35 µg/ml and 150 µg/ml of insulin, such as between 0.35 µg/ml and 100 µg/ml of insulin, such as between 0.35 µg/ml and 50 µg/ml of insulin, such as between 0.35 µg/ml and 25 µg/ml of insulin, such as between 0.35 µg/ml and 10 µg/ml of insulin, such as between 0.35 µg/ml and 1 µg/ml of insulin, such as between 0.5 µg/ml and 1 µg/ml of insulin, such as between 1 µg/ml and 350 µg/ml of insulin, such as between 10 µg/ml and 350 µg/ml of insulin, such as between 25 µg/ml and 350 µg/ml of insulin, such as between 50 µg/ml and 350 µg/ml of insulin, such as between 100 µg/ml and 350 µg/ml of insulin, such as between 150 µg/ml and 350 µg/ml of insulin, such as between 200 µg/ml and 350 µg/ml of insulin, such as between 250 µg/ml and 350 µg/ml of insulin, such as between 300 µg/ml and 350 µg/ml of insulin.

In some embodiments of the present disclosure the composition comprises between 0.006 µmol/ml and 6 mol/ml of insulin, such as between 0.01 µmol/ml and 6 mol/ml of insulin, such as between 0.05 µmol/ml and 6 mol/ml of insulin, such as between 0.1 µmol/ml and 6 mol/ml of insulin, such as between 0.5 µmol/ml and 6 mol/ml of insulin, such as between 1 µmol/ml and 6 mol/ml of insulin, such as between 10 µmol/ml and 6 mol/ml of insulin, such as between 50 µmol/ml and 6 mol/ml of insulin, such as between 100 µmol/ml and 6 mol/ml of insulin, such as between 1 mmol/ml and 6 mol/ml of insulin, such as between 10 mmol/ml and 6 mol/ml of insulin, such as between 50 mmol/ml and 6 mol/ml of insulin, such as between 100 mmol/ml and 6 mol/ml of insulin, such as between 1 mol/ml and 6 mol/ml of insulin, such as between 2 mol/ml and 6 mol/ml of insulin, such as between 3 mol/ml and 6 mol/ml of insulin, such as between 4 mol/ml and 6 mol/ml of insulin, such as between 5 mol/ml and 6 mol/ml of insulin, such as between 0.006 µmol/ml and 5 mol/ml of insulin, such as between 0.006 µmol/ml and 4 mol/ml of insulin, such as between 0.006 µmol/ml and 3 mol/ml of insulin, such as between 0.006 µmol/ml and 2 mol/ml of insulin, such as between 0.006 µmol/ml and 1 mol/ml of insulin, such as between 0.006 µmol/ml and 100 mmol/ml of insulin, such as between 0.006 µmol/ml and 50 mmol/ml of insulin, such as between 0.006 µmol/ml and 10 mmol/ml of insulin, such as between 0.006 µmol/ml and 1 mmol/ml of insulin, such as between 0.006 µmol/ml and 100 µmol/ml of insulin, such as between 0.006 µmol/ml and 50 µmol/ml of insulin, such as between 0.006 µmol/ml and 10 µmol/ml of insulin, such as between 0.006 µmol/ml and 1 µmol/ml of insulin, such as between 0.006 µmol/ml and 0.5 µmol/ml of insulin, such as between 0.006 µmol/ml and 0.1 µmol/ml of insulin, such as between 0.006 µmol/ml and 0.05 µmol/ml of insulin, such as between 0.006 µmol/ml and 0.01 µmol/ml of insulin.

In some embodiments of the present disclosure the composition has a volume comprised between 0 and 500 ml, such as between 0 and 450 ml, such as between 0 and 400 ml, such as between 0 and 350 ml, such as between 0 and 300 ml, such as between 0 and 250 ml, such as between 0 and 200 ml, such as between 0 and 150 ml, such as between 0 and 100 ml, such as between 0 and 50 ml.

In some embodiments of the present disclosure the total dose of insulin per day is between 0.01 and 1000 IU, such as between 0.01 IU and 900 IU, such as between 0.01 IU and 800 IU, such as between 0.01 IU and 800 IU, such as between 0.01 IU and 700 IU, such as between 0.01 IU and 600 IU, such as between 0.01 IU and 500 IU, such as between 0.01 IU and 400 IU, such as between 0.01 IU and 300 IU, such as between 0.01 IU and 200 IU, such as between 0.01 IU and 100 IU, such as between 0.01 IU and 50 IU, such as between 0.01 IU and 25 IU, such as between 25 IU and 1000 IU, such as between 50 IU and 1000 IU, such as between 100 IU and 1000 IU, such as between 200 IU and 1000 IU, such as between 300 IU and 1000 IU, such as between 400 IU and 1000 IU, such as between 500 IU and 1000 IU, such as between 600 IU and 1000 IU, such as between 700 IU and 1000 IU, such as between 800 IU and 1000 IU.

In some embodiments of the present disclosure the total dose of insulin per day is between 0.35 µg and 35 g of insulin, such as between 0.35 µg and 30 g of insulin, such as between 0.35 µg and 25 g of insulin, such as between 0.35 µg and 20 g of insulin, such as between 0.35 µg and 15 g of insulin, such as between 0.35 µg and 10 g of insulin, such as between 0.35 µg and 5 g of insulin, such as between 0.35 µg and 1 g of insulin, such as between 0.35 µg and 100 mg of insulin, such as between 0.35 µg and 50 mg of insulin, such as between 0.35 µg and 1 mg of insulin, such as between 0.35 µg and 100 µg of insulin, such as between 0.35 µg and 50 µg of insulin, such as between 0.35 µg and 10 µg of insulin, such as between 0.35 µg and 1 µg of insulin, such as between 1 µg and 35 g of insulin, such as between 10 µg and 35 g of insulin, such as between 50 µg and 35 g of insulin, such as between 100 µg and 35 g of insulin, such as between 1 mg and 35 g of insulin, such as between 10 mg and 35 g of insulin, such as between 50 mg and 35 g of insulin, such as between 100 mg and 35 g of insulin, such as between 1 g and 35 g of insulin, such as between 10 g and 35 g of insulin, such as between 20 g and 35 g of insulin.

In some embodiments of the present disclosure the total dose of insulin per day is between 0.006 µmol and 6 mol of insulin, such as between 0.006 µmol and 1 mol of insulin, such as between 0.006 µmol and 100 mmol of insulin, such as between 0.006 µmol and 50 mmol of insulin, such as between 0.006 µmol and 10 mmol of insulin, such as between 0.006 µmol and 1 mmol of insulin, such as between 0.006 µmol and 100 µmol of insulin, such as between 0.006 µmol and 50 µmol of insulin, such as between 0.006 µmol and 10 µmol of insulin, such as between 0.006 µmol and 1 µmol of insulin, such as between 0.006 µmol and 0.1 µmol of insulin, such as between 0.006 µmol and 0.01 µmol of insulin, such as between 0.01 µmol and 6 mol of insulin, such as between 0.05 µmol and 6 mol of insulin, such as between 0.1 µmol and 6 mol of insulin, such as between 0.5 µmol and 6 mol of insulin, such as between 1 µmol and 6 mol of insulin, such as between 10 µmol and 6 mol of insulin, such as between 50 µmol and 6 mol of insulin, such as between 100 µmol and 6 mol of insulin, such as between 1 mmol and 6 mol of insulin, such as between 10 mmol and 6 mol of insulin, such as between 50 mmol and 6 mol of insulin, such as between 100 mmol and 6 mol of insulin, such as between 1 mol and 6 mol of insulin, such as between 2 mol and 6 mol of insulin, such as between 3 mol and 6 mol of insulin, such as between 4 mol and 6 mol of insulin, such as between 5 mol and 6 mol of insulin.

Therefore, the composition comprising insulin as disclosed herein can be administered to the subject in need thereof once daily, such as twice daily, such as three times daily. The composition comprising insulin as disclosed herein can also be administered to the subject in need thereof once each other day, such as three times a week, such as twice a week, such as once a week.

IBDs are characterized by acute phases and remission phases and therefore easily become chronic diseases. Treatment of IBDs is usually prolonged in time.

In some embodiments of the present disclosure the composition is administered to the subject in need thereof over a period of at least 3 weeks, such as over a period of at least 4 weeks, such as over a period of at least 5 weeks, as over a period of at least 6 weeks, as over a period of at least 7 weeks.

In some embodiments of the present disclosure the composition is administered to the subject in need thereof over a period comprised between 3 weeks and 3 months, such as between 3 weeks and 4 months, such as between 3 weeks and 5 months, such as between 3 weeks and 6 months, such as between 3 weeks and 7 months, such as between 3 weeks and 8 months, such as between 3 weeks and 9 months, such as between 3 weeks and 10 months, such as between 3 weeks and 11 months, such as between 3 weeks and 12 months.

In some embodiments of the present disclosure the composition is administered to the subject in need thereof over a period of 1 year or longer than 1 year.

In some embodiments of the present disclosure the composition is administered to the subject in need thereof lifelong.

The duration of treatment will depend on several factors, for example on the response of the subject to rectally administered insulin as well as to other treatments commonly used for IBDs. The duration of the treatment will depend also in the severity of the disease as well as on the stage of the disease. If the purpose of the treatment is to keep the disease in a remission phase, the treatment may be carried on for a long period of time, such as months or years or lifelong. As the rectally administered insulin does not usually have systemic effects, no side effects are expected when it is administered for long periods of time.

Formulation

Insulin for rectal administration can be formulated in various ways, as will be apparent to the skilled person. The compositions for rectal administration disclosed herein may be formulated with appropriate excipients so as to provide emollient or drying effect to the rectal mucosa. Suitable excipients such as, but not limited to, vehicle (such as aqueous or non-aqueous vehicle), preservatives, surfactants, emulsifiers, mineral oils, propellants, thickening agents, lubricants, preservatives, pH adjusting agents, chelating agents, emollients and/or humectants, permeation enhancers, suspension-forming agents or mucoadhesive agents or combinations thereof, may be used for formulating the compositions for rectal administration disclosed herein.

Usually insulin or a pharmaceutically acceptable salt thereof will be dissolved in a suitable solvent, for example phosphate buffered saline or isotonic sodium chloride, among others.

In some embodiments of the present disclosure the composition is in the form of a rectal foam, a gel, an enema, an aerosol, an ointment, a cream, a gastric lavage, a suppository, a rectal lavage using a catheter, a mechanical insulin release device orally ingested or a pharmaceutical colonic release system, wherein the insulin is released in the large intestine. For example, the rectal lavage can be administered using a catheter placed in the rectum or by using a catheter placed, during surgery, in the distal ileum or in the caecum.

A mechanical insulin release device orally ingested is for example a microdevice, or any suitable device that can be ingested by a subject in need without complications, that releases insulin only when it reaches the large intestine, for example when it reaches the colon. Examples of such devices are found in Woods et al., 2015, A pharmaceutical colonic release system is a pharmaceutical formulation that releases the active agent, insulin within the meaning of the present disclosure, at a certain time or under certain conditions. It can for example be a pharmaceutical composition that disintegrates, and so releases the active agent, a pre-determined period of time after administration in response to the in vivo conditions.

In some embodiments of the present disclosure the composition is administered via a percutaneous catheter, via an intraintestinal catheter, endoscopically, or via a mechanical intraluminal device.

In some embodiments of the present disclosure the composition further comprises a protease inhibitor and/or an antibiotic. In fact, protease inhibitor may increase the in vivo stability of insulin and so prolong the in vivo half-life and effects. Antibiotics can also prolong the effects of insulin. In fact, the colonic degradation of proteins is to a large extent due to bacterial proteases. Thus by lowering the colonic bacterial content with administration of antibiotics, preferably local administration, the amounts of bacterial proteases are reduced and the degradation of luminal proteins are accordingly also reduced.

In some embodiments of the present disclosure the composition further comprises one or more additional compounds that improve the therapeutic effects of rectally administered insulin.

The formulation disclosed herein is for "rectal administration" of insulin, which corresponds to administration of insulin to the rectum, or more in general to the large intestine, of a subject in need thereof and wherein said insulin acts almost exclusively on the cells of the large intestine. Accordingly, a rectally administered pharmaceutically active ingredient is not adsorbed by the intestine and thus it is not taken up into the blood stream of the treated subject.

Further Treatment

Rectal administration of insulin for treatment of IBDs and/or inflammation induced colorectal tumour and/or cancer can be supplement by an additional treatment, for example by a therapy currently used for treatment of IBDs and/or inflammation induced colorectal tumour and/or cancer.

Therefore, in some embodiments of the present disclosure, the composition is co-administered with a further treatment for inflammatory bowel disease and/or inflammation-induced colorectal tumour and/or cancer.

Currently, concerning Crohn's disease, remission is induced, in the cases with exacerbation with mild to moderate activity, by administration of budesonide or mesalazine (ileocecal involvement), or sulfasalazine (colonic involvement). In the cases where exacerbation with severe activity is observed, prednisolone is administered in order to induce remission. The drugs administered in the state of the art to maintain remission are azathioprine, methotrexate, 6-mercaptopurine, infliximab, anti-TNFα or anti-integrin antibodies optionally supplemented with azathioprine or adalimumab, or vedolizumab. Drugs administered for induction of remission, and so during acute phase, in Crohn's disease are budesonide, mesalazine, glucocorticoids, sulfasalazine, anti-TNFα, anti-integrins or other antibodies. For ulcerative colitis, mesalazine optionally supplemented with steroids or glucocorticoids, or tacrolimus are administered during attacks, while cyclosporine, infliximab, tacrolimus, or mesalazine followed by *E. coli* Nissle then azathioprine or 6-mercaptopurine and anti-TNFα or anti-integrin antibodies.

Therefore, in some embodiments of the present disclosure, the further treatment comprises or consists of administration of a steroid, a corticosteroid, an aminosalicylate, an anti-TNFα antibody, an anti-integrin antibody, an immunosuppressive drug, a calcineurin inhibitor, or a probiotic.

In some embodiments of the present disclosure, the further treatment comprises or consists of administration of budesonide, mesalazine, sulfasalazine, 5-aminosalicylic acid (5-ASA), infliximab, adalimumab, golimumab, vedolizumab, a thiopurine drug such as azathioprine or 6-mercaptopurine, methotrexate, cyclosporine, tacrolimus, or viable non-pathogenic bacterial strain *Escherichia coli* Nissle 1917 (*E. coli* Nissle).

Some of the above mentioned drugs are preferably administered during the acute phase and/or during relapse of the IBD and/or inflammation-induced colorectal tumour and/or cancer, whereas some other drugs are preferably administered during the remission phase relapse of the IBD and/or inflammation-induced colorectal tumour and/or cancer. Moreover, some drugs are suitable for treatment of both acute phase/relapse and remission of the IBD and/or inflammation-induced colorectal tumour and/or cancer.

In some embodiments of the present disclosure, the composition comprising insulin is co-administered with a further treatment to a subject suffering from or suspected of suffering from an inflammatory bowel disease and/or inflammation-induced colorectal tumour and/or cancer during the acute phase and/or in case of relapse and wherein the further treatment comprises or consists of administration of a steroid, a corticosteroid, an aminosalicylate, an anti-TNFα antibody, an anti-integrin antibody, an immunosuppressive drug, or a calcineurin inhibitor.

In some embodiments of the present disclosure, the composition comprising insulin is co-administered with a further treatment to a subject suffering from or suspected of suffering from an inflammatory bowel disease and/or inflammation-induced colorectal tumour and/or cancer during the remission phase and wherein the further treatment comprises or consists of administration of an aminosalicylate, an anti-TNFα antibody, an anti-integrin antibody, an immunosuppressive drug, a calcineurin inhibitor, or a probiotic.

In some embodiments of the present disclosure, the further treatment is rectal, oral, sublingual, nasal, intravenous, intramuscular, or subcutaneous. For example, any one of the above mentioned drugs may be administered rectally, orally, sublingually, nasally, intravenously, intramuscularly or subcutaneously to a subject suffering from or suspected of suffering from an IBD and/or inflammation-induced colorectal tumour and/or cancer in the same period of time as insulin is administered rectally to the same subject according to the present disclosure.

For example rectal administration of insulin can be combined with oral administration of 5-aminosalicylic acid or with both oral and rectal administration of 5-aminosalicylic acid.

Rectal administration of insulin can also be combined with oral or rectal administration of corticosteroids, or with oral administration of corticosteroids and rectal administration of 5-aminosalicylic acid, or with oral administration of both corticosteroids and 5-aminosalicylic acid, or with rectal administration of corticosteroids and oral administration of 5-aminosalicylic acid.

Rectal administration of insulin can also be combined with administration of an anti-TNFα antibody, for example infliximab, or with administration of a combination of an anti-TNFα antibody and a thiopurine. Rectal administration of insulin can also be combined with administration of an anti-TNFα antibody, for example infliximab, and a corticosteroid, or with administration of a combination of an anti-TNFα antibody, a corticosteroid and a thiopurine.

Rectal administration of insulin can also be combined with administration of an anti-integrin antibody, for example vedolizumab, or with administration of a combination of an anti-integrin antibody and a thiopurine. Rectal administration of insulin can also be combined with administration of an anti-integrin antibody, for example vedolizumab, and a corticosteroid, or with administration of a combination of an anti-integrin antibody, a corticosteroid and a thiopurine.

The further treatment may be administered for a longer period of time, for the same period of time or for a shorter period of time as the rectal administration of insulin.

In some embodiments of the present disclosure, a subject suffering from or suspected of suffering from Crohn's disease is further treated with administration of budesonide and/or steroids and/or aminosalicylates such as mesalazine, sulfasalazine and 5-aminosalicylic acid (5-ASA), and/or an anti-TNFα antibody (for example infliximab or adalimumab) and/or an anti-integrin antibody (for example vedolizumab) and/or an immunosuppressive drug, such as the thiopurine drugs azathioprine and/or 6-mercaptopurine, and/or methotrexate.

In some embodiments of the present disclosure, a subject suffering from or suspected of suffering from Crohn's disease is further treated during acute phase and/or in case of relapse with administration of budesonide and/or steroids and/or aminosalicylates such as mesalazine, sulfasalazine and 5-aminosalicylic acid (5-ASA), and/or an anti-TNFα antibody (for example infliximab or adalimumab) and/or an anti-integrin antibody (for example vedolizumab).

In some embodiments of the present disclosure, a subject suffering from or suspected of suffering from Crohn's disease is further treated during remission phase with administration of an immunosuppressive drug, such as the thiopurine drugs azathioprine and/or 6-mercaptopurine, and/or methotrexate and/or aminosalicylates such as mesalazine, sulfasalazine and 5-aminosalicylic acid (5-ASA), and/or an anti-TNFα antibody (for example infliximab or adalimumab).

In some embodiments of the present disclosure, a subject suffering from or suspected of suffering from ulcerative colitis is further treated with administration of aminosalicylates such as mesalazine, sulfasalazine and 5-aminosalicylic acid (5-ASA) and/or steroids and/or corticosteroids such as prednisone and/or calcineurin inhibitors such as cyclosporine and tacrolimus and/or an anti-TNFα antibody (for example infliximab or adalimumab or golimumab) and/or an anti-integrin antibody (for example vedolizumab).

In some embodiments of the present disclosure, a subject suffering from or suspected of suffering from ulcerative colitis is further treated during the acute phase and/or in case of relapse with administration of aminosalicylates such as mesalazine, sulfasalazine and 5-aminosalicylic acid (5-ASA) and/or steroids and/or corticosteroids such as prednisone and/or calcineurin inhibitors such as cyclosporine and tacrolimus and/or an anti-TNFα antibody (for example infliximab or adalimumab or golimumab) and/or an anti-integrin antibody (for example vedolizumab).

In some embodiments of the present disclosure, a subject suffering from or suspected of suffering from ulcerative colitis is further treated during the remission phase with administration of aminosalicylates such as mesalazine, sulfasalazine and 5-aminosalicylic acid (5-ASA) and/or steroids and/or corticosteroids such as prednisone and/or calcineurin inhibitors such as cyclosporine and tacrolimus and/or an anti-TNFα antibody (for example infliximab or adalimumab or golimumab) and/or an anti-integrin antibody (for example vedolizumab) and/or the probiotic viable non-pathogenic bacterial strain *Escherichia coli* Nissle 1917 (*E. coli* Nissle).

In some embodiments of the present disclosure, no steroids or corticosteroids are administered to a subject in need thereof during remission phase. In fact, steroids and corticosteroids may have adverse effects and their prolonged use should be avoided when possible.

Items

1. A composition comprising a therapeutically effective amount of insulin or a pharmaceutically acceptable salt thereof for use in a method of treatment of inflammatory bowel disease and/or inflammation-induced colorectal tumour and/or cancer, wherein the composition is administered rectally to a subject in need thereof.

2. A composition comprising a therapeutically effective amount of insulin or a pharmaceutically acceptable salt thereof for use in a method of treatment of inflammatory bowel disease and/or inflammation-induced colorectal tumour and/or cancer, wherein the composition is administered locally to the large intestine to a subject in need thereof.

3. The composition for the use of any one of the preceding items, wherein the composition is administered rectally to a subject in need thereof and wherein the composition increases the expression of Car3 mRNA in epithelial cells of the large intestine.

4. The composition for the use of any one of the preceding items, wherein the composition comprises between 0.01 IU and 1000 IU, such as between 0.01 IU and 900 IU, such as between 0.01 IU and 800 IU, such as between 0.01 IU and 800 IU, such as between 0.01 IU and 700 IU, such as between 0.01 IU and 600 IU, such as between 0.01 IU and 500 IU, such as between 0.01 IU and 400 IU, such as between 0.01 IU and 300 IU, such as between 0.01 IU and 200 IU, such as between 0.01 IU and 100 IU, such as between 0.01 IU and 50 IU, such as between 0.01 IU and 25 IU, such as between 25 IU and 1000 IU, such as between 50 IU and 1000 IU, such as between 100 IU and 1000 IU, such as between 200 IU and 1000 IU, such as between 300 IU and 1000 IU, such as between 400 IU and 1000 IU, such as between 500 IU and 1000 IU, such as between 600 IU and 1000 IU, such as between 700 IU and 1000 IU, such as between 800 IU and 1000 IU.

5. The composition for the use of any one of the preceding items, wherein the composition comprises between 0.35 µg and 35 g of insulin, such as between 0.35 µg and 30 g of insulin, such as between 0.35 µg and 25 g of insulin, such as between 0.35 µg and 20 g of insulin, such as between 0.35 µg and 15 g of insulin, such as between 0.35 µg and 10 g of insulin, such as between 0.35 µg and 5 g of insulin, such as between 0.35 µg and 1 g of insulin, such as between 0.35 µg and 100 mg of insulin, such as between 0.35 µg and 50 mg of insulin, such as between 0.35 µg and 1 mg of insulin, such as between 0.35 µg and 100 µg of insulin, such as between 0.35 µg and 50 µg of insulin, such as between 0.35 µg and 10 µg of insulin, such as between 0.35 µg and 1 µg of insulin, such as between 1 µg and 35 g of insulin, such as between 10 µg and 35 g of insulin, such as between 50 µg and 35 g of insulin, such as between 100 µg and 35 g of insulin, such as between 1 mg and 35 g of insulin, such as between 10 mg and 35 g of insulin, such as between 50 mg and 35 g of insulin, such as between 100 mg and 35 g of insulin, such as between 1 g and 35 g of insulin, such as between 10 g and 35 g of insulin, such as between 20 g and 35 g of insulin.

6. The composition for the use of any one of the preceding items, wherein the composition comprises between 0.006 µmol and 6 mol of insulin, such as between 0.006 µmol and 1 mol of insulin, such as between 0.006 µmol and 100 mmol of insulin, such as between 0.006 µmol and 50 mmol of insulin, such as between 0.006 µmol and 10 mmol of insulin, such as between 0.006 µmol and 1 mmol of insulin, such as between 0.006 µmol and 100 µmol of insulin, such as between 0.006 µmol and 50 µmol of insulin, such as between 0.006 µmol and 10 µmol of insulin, such as between 0.006 µmol and 1 µmol of insulin, such as between 0.006 µmol and 0.1 µmol of insulin, such as between 0.006 µmol and 0.01 µmol of insulin, such as between 0.01 µmol and 6 mol of insulin, such as between 0.05 µmol and 6 mol of insulin, such as between 0.1 µmol and 6 mol of insulin, such as between 0.5 µmol and 6 mol of insulin, such as between 1 µmol and 6 mol of insulin, such as between 10 µmol and 6 mol of insulin, such as between 50 µmol and 6 mol of insulin, such as between 100 µmol and 6 mol of insulin, such as between 1 mmol and 6 mol of insulin, such as between 10 mmol and 6 mol of insulin, such as between 50 mmol and 6 mol of insulin, such as between 100 mmol and 6 mol of insulin, such as between 1 mol and 6 mol of insulin, such as between 2 mol and 6 mol of insulin, such as between 3 mol and 6 mol of insulin, such as between 4 mol and 6 mol of insulin, such as between 5 mol and 6 mol of insulin.

7. The composition for the use of any one of the preceding items, wherein the composition comprises between 0.01 IU/ml and 10 IU/ml, such as between 0.01 IU/ml and 9 IU/ml, such as between 0.01 IU/ml and 8 IU/ml, such as between 0.01 IU/ml and 7 IU/ml, such as between 0.01 IU/ml and 6 IU/ml, such as between 0.01 IU/ml and 5 IU/ml, such as between 0.01 IU/ml and 4 IU/ml, such as between 0.01 IU/ml and 3 IU/ml, such as between 0.01 IU/ml and 2 IU/ml, such as between 0.01 IU/ml and 1 IU/ml, such as between 0.01 IU/ml and 0.1 IU/ml, such as between 0.1 IU/ml and 10 IU/ml, such as between 1 IU/ml and 10 IU/ml, such as between 2 IU/ml and 10 IU/ml, such as between 3 IU/ml and 10 IU/ml, such as between 4 IU/ml and 10 IU/ml, such as between 5 IU/ml and 10 IU/ml, such as between 6 IU/ml and 10 IU/ml, such as between 7 IU/ml and 10 IU/ml, such as between 8 IU/ml and 10 IU/ml, such as between 9 IU/ml and 10 IU/ml.

8. The composition for the use of any one of the preceding items, wherein the composition has a volume between 0 and 500 ml, such as between 0 and 450 ml, such as between 0 and 400 ml, such as between 0 and 350 ml, such as between 0 and 300 ml, such as between 0 and 250 ml, such as between 0 and 200 ml, such as between 0 and 150 ml, such as between 0 and 100 ml, such as between 0 and 50 ml.

9. The composition for the use of any one of the preceding items, wherein the total dose of insulin per day is between 0.01 IU and 1000 IU, such as between 0.01 IU and 900 IU, such as between 0.01 IU and 800 IU, such as between 0.01 IU and 800 IU, such as between 0.01 IU and 700 IU, such as between 0.01 IU and 600 IU, such as between 0.01 IU and 500 IU, such as between 0.01 IU and 400 IU, such as between 0.01 IU and 300 IU, such as between 0.01 IU and 200 IU, such as between 0.01 IU and 100 IU, such as between 0.01 IU and 50 IU, such as between 0.01 IU and 25 IU, such as between 25 IU and 1000 IU, such as between 50 IU and 1000 IU, such as between 100 IU and 1000 IU, such as between 200 IU and 1000 IU, such as between 300 IU and 1000 IU, such as between 400 IU and 1000 IU, such as between 500 IU and 1000 IU, such as between 600 IU and 1000 IU, such as between 700 IU and 1000 IU, such as between 800 IU and 1000 IU.

10. The composition for the use of any one of the preceding items, wherein the composition is administered to the subject in need thereof over a period of at least 3 weeks, such as over a period of at least 4 weeks, such as over a period of at least 5 weeks, as over a period of at least 6 weeks, as over a period of at least 7 weeks, such as lifelong.

11. The composition for the use of any one of the preceding items, wherein the composition is administered to the subject in need thereof during the remission phase of the inflammatory bowel disease and/or inflammation-induced colorectal tumour and/or cancer for a period between 3 weeks and 3 months, such as between 3 weeks and 4 months, such as between 3 weeks and 5 months, such as between 3 weeks and 6 months, such as between 3 weeks and 7 months, such as between 3 weeks and 8 months, such as between 3 weeks and 9 months, such as between 3 weeks and 10 months, such as between 3 weeks and 11 months, such as between 3 weeks and 12 months, such as between 3 weeks and 18 months, such as between 3 weeks and 24 months.

12. The composition for the use of any one of the preceding items, wherein said composition is in the form of a rectal foam, a gel, an enema, an aerosol, an ointment, a cream, a gastric lavage, a suppository, a rectal lavage using a catheter, a mechanical insulin release device orally ingested or a pharmaceutical colonic release system, wherein the insulin is released in the large intestine.

13. The composition for the use of any one of the preceding items, wherein said composition is administered via a percutaneous catheter, via an intraintestinal catheter, endoscopically, or via a mechanical intraluminal device.

14. The composition for the use of any one of the preceding items, wherein the mechanical insulin release device orally ingested is a microdevice.

15. The composition for the use of any one of the preceding items, wherein the inflammatory bowel disease is selected from the group consisting of ulcerative colitis, diversion colitis, Behçet's disease, indeterminate colitis, left sided colitis, microscopic colitis such as collagenous colitis or lymphocytic colitis, Crohn's disease, noninfective colitis and pouchitis.

16. The composition for the use of any one of the preceding items, wherein the inflammatory bowel disease is selected from the group consisting of ulcerative colitis, diversion colitis, Behçet's disease, indeterminate colitis, left sided colitis, Crohn's disease, noninfective colitis and pouchitis.

17. The composition for the use of any one of the preceding items, wherein the composition is administered to a subject suffering from or suspected of suffering from an inflammatory bowel disease and/or inflammation-induced colorectal tumour and/or cancer during the acute phase and/or during relapse of the disease.

18. The composition for the use of any one of the preceding items, wherein the composition is administered to a subject suffering from or suspected of suffering from an inflammatory bowel disease and/or inflammation-induced colorectal tumour and/or cancer during the remission phase of the disease.

19. The composition for the use of any one of the preceding items, wherein the composition is administered to a subject suffering from or suspected of suffering from an inflammatory bowel disease during the acute phase and/or during relapse of the disease.

20. The composition for the use of any one of the preceding items, wherein the composition is administered to a subject suffering from or suspected of suffering from an inflammatory bowel disease during the remission phase of the disease.

21. The composition for the use of any one of the preceding items, wherein the composition is administered to a subject suffering from or suspected of suffering from inflammation-induced colorectal tumour and/or cancer during the acute phase and/or during relapse of the disease.
22. The composition for the use of any one of the preceding items, wherein the composition is administered to a subject suffering from or suspected of suffering from during the remission phase of the disease.
23. The composition for the use of any one of the preceding items, wherein the composition is administered to a subject suffering from or suspected of suffering from mild to moderate ulcerative colitis.
24. The composition for the use of any one of the preceding items, wherein the composition is administered to a subject suffering from or suspected of suffering from mild to moderate ulcerative colitis during the acute phase and/or during relapse of the disease.
25. The composition for the use of any one of the preceding items, wherein the composition is administered to a subject suffering from or suspected of suffering from mild to moderate ulcerative colitis during the remission phase of the disease.
26. The composition for the use of any one of the preceding items, wherein the composition is administered to a subject in need thereof, wherein the subject presents one or more of the following symptoms: abdominal pain, vomiting, chronic diarrhoea, rectal bleeding, severe internal cramps/muscle spasms in the region of the pelvis, weight loss, deep geographic and serpiginous ulcers, continuous ulcer, transmural inflammation, mucosal inflammation, stenosis, granulomas on biopsy (for example non-necrotizing non-peri-intestinal crypt granulomas), high levels of faecal calprotectin, anaemia, thrombocytosis, architectonic abnormalities of the rectal tissue on histological examination, fistulae or abscesses to any segment of the gastrointestinal tract, toxic megacolon.
27. The composition for the use of any of the preceding items, wherein the composition is administered to a subject who has been diagnosed with an inflammatory bowel disease and/or inflammation-induced colorectal tumour and/or cancer.
28. The composition for the use of any of the preceding items, wherein the composition is capable of reducing inflammation of epithelial cells of the colon.
29. The composition for the use of any one of the preceding items, wherein the composition is capable of reducing expression of COX2 mRNA.
30. The composition for the use of any of the preceding items, wherein the composition is capable of increasing the expression of Carbonic anhydrase 3 (Car3) mRNA.
31. The composition for the use of any of the preceding items, wherein the composition is capable of improving epithelial ion transport in the large intestine.
32. The composition for the use of any of the preceding items, wherein the composition does not cause cell proliferation in the small intestine.
33. The composition for the use of any one of the preceding items, wherein the composition further comprises a protease inhibitor and/or an antibiotic.
34. The composition for the use of any one of the preceding items, wherein the composition is co-administered with a further treatment for inflammatory bowel disease and/or inflammation-induced colorectal tumour and/or cancer.
35. The composition for the use of item 34, wherein the further treatment is rectal, oral, sublingual, nasal, intravenous, intramuscular, or subcutaneous.
36. The composition for the use of any one of items 34 to 35, wherein the further treatment comprises or consists of administration of a steroid, a corticosteroid, an aminosalicylate, an anti-TNFα antibody, an anti-integrin antibody, an immunosuppressive drug, a calcineurin inhibitor, or a probiotic.
37. The composition for the use of any one of items 34 to 36, wherein the further treatment comprises or consists of administration of budesonide, mesalazine, sulfasalazine, 5-aminosalicylic acid (5-ASA), infliximab, adalimumab, golimumab, vedolizumab, a thiopurine drug such as azathioprine or 6-mercaptopurine, methotrexate, cyclosporine, tacrolimus, or viable non-pathogenic bacterial strain *Escherichia coli* Nissle 1917 (*E. coli* Nissle).
38. The composition for the use of any one of items 34 to 37, wherein the composition is co-administered with a further treatment to a subject suffering from or suspected of suffering from an inflammatory bowel disease and/or inflammation-induced colorectal tumour and/or cancer during the acute phase and/or in case of relapse and wherein the further treatment comprises or consists of administration of a steroid, a corticosteroid, an aminosalicylate, an anti-TNFα antibody, an anti-integrin antibody, an immunosuppressive drug, or a calcineurin inhibitor.
39. The composition for use of any one of items 34 to 38, wherein the composition is co-administered with a further treatment to a subject suffering from or suspected of suffering from an inflammatory bowel disease and/or inflammation-induced colorectal tumour and/or cancer during the remission phase and wherein the further treatment comprises or consists of administration of an aminosalicylate, an anti-TNFα antibody, an anti-integrin antibody, an immunosuppressive drug, a calcineurin inhibitor, or a probiotic.
40. A method for treatment of an inflammatory bowel disease and/or inflammation-induced colorectal tumour and/or cancer in a subject in need thereof, the method comprising rectal administration of a composition comprising a therapeutically effective amount of insulin or a pharmaceutically acceptable salt thereof.
41. A method for treatment of an inflammatory bowel disease and/or inflammation-induced colorectal tumour and/or cancer in a subject in need thereof, the method comprising administration of a composition comprising a therapeutically effective amount of insulin or a pharmaceutically acceptable salt thereof locally to the large intestine of said subject.
42. A method of reducing weight loss in a subject suffering from or suspected of suffering from an inflammatory bowel disease and/or inflammation-induced colorectal tumour and/or cancer, the method comprising rectal administration of a composition comprising a therapeutically effective amount of insulin or a pharmaceutically acceptable salt thereof.
43. A method of reducing weight loss in a subject suffering from or suspected of suffering from an inflammatory bowel disease and/or inflammation-induced colorectal tumour and/or cancer, the method comprising administration of a composition comprising a therapeutically effective amount of insulin or a pharmaceutically acceptable salt thereof locally to the large intestine of said subject.
44. A method of healing colonic mucosa in a subject suffering from or suspected of suffering from an inflammatory bowel disease and/or inflammation-induced colorectal tumour and/or cancer, the method comprising rectal administration of a composition comprising a therapeutically effective amount of insulin or a pharmaceutically acceptable salt thereof.
45. A method of healing colonic mucosa in a subject suffering from or suspected of suffering from an inflammatory bowel disease and/or inflammation-induced colorectal tumour and/or cancer, the method comprising administration of a composition comprising a therapeutically effective amount of insulin or a pharmaceutically acceptable salt thereof locally to the large intestine of said subject.
46. The method of any one of items 40 and 43, wherein the composition is as defined in any one of items 1 to 39.
47. A composition comprising a therapeutically effective amount of insulin or a pharmaceutically acceptable salt thereof for increasing the expression of Car3 mRNA in epithelial cells of the large intestine.
48. An agent capable of increasing the expression of Car3 mRNA in epithelial cells of the large intestine for use in in a method of treatment of inflammatory bowel disease and/or inflammation-induced colorectal tumour and/or cancer, wherein the composition is administered rectally to a subject in need thereof.
49. An agent capable of increasing the expression of Car3 mRNA in epithelial cells of the large intestine for use in in a method of treatment of inflammatory bowel disease and/or inflammation-induced colorectal tumour and/or cancer, wherein the composition is administered locally to the large intestine to a subject in need thereof.
50. A method of treatment of inflammatory bowel disease and/or inflammation-induced colorectal tumour and/or cancer, the method comprising administering an agent capable of increasing the expression of Car3 mRNA epithelial cells of the large intestine.

EXAMPLES

Example 1. Insulin Signalling Inhibits Colitis and Tumour Development

In the azoxymethane and dextran sulphate sodium (AOM/DSS) carcinogenesis/colitis model, colitis is induced by DSS which promotes AOM induced tumours. This AOM/DSS model was used on mice having intestinal specific inactivation of the insulin receptor. These mice were obtained by crossing mice (B6.129S4(FVB)-Insrtm1Khn/J) with loxP sites flanking exon 4 in the insulin receptor gene with mice (B6.Cg-Tg(Vil-cre)997Gum/J) expressing the cre-recombinase under the villin promoter (both mice were obtained commercially from the Jackson Laboratory).

Figure 2:
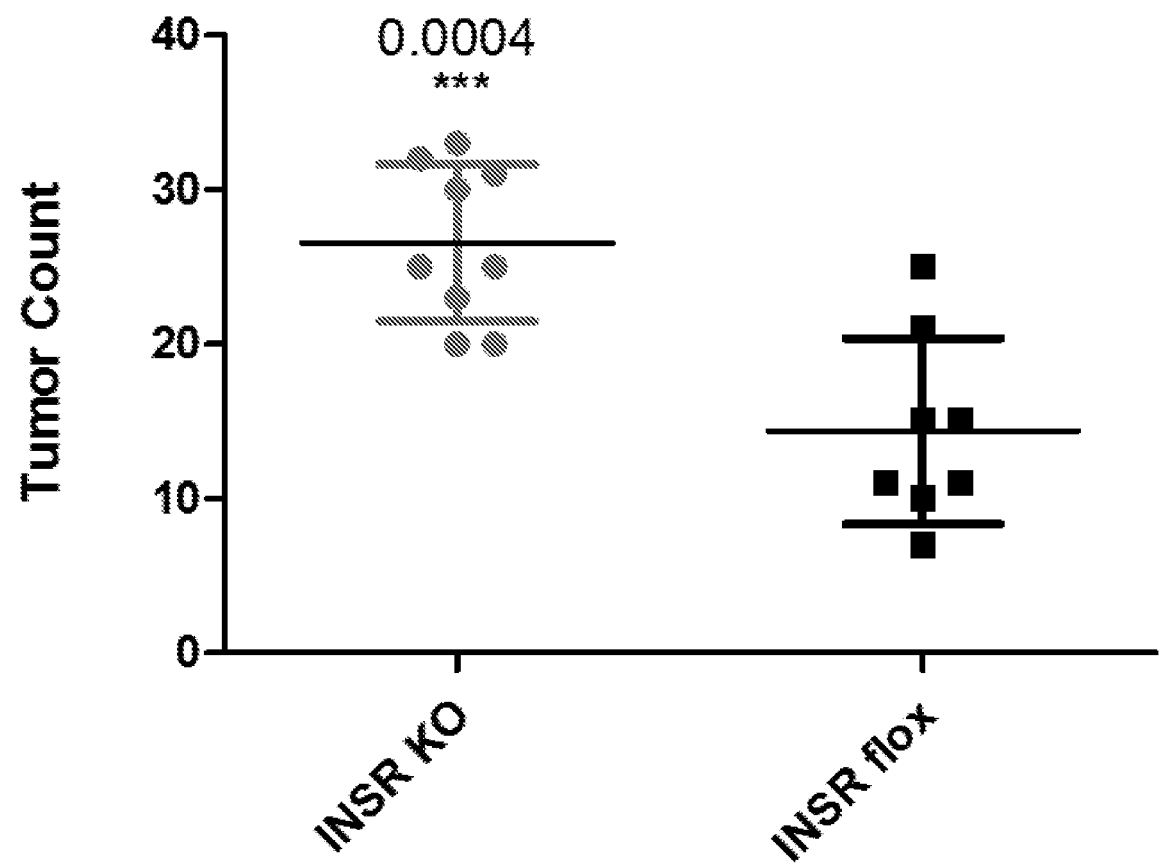
FIG. 2. Mice with intestinal specific inactivation of the insulin receptor (INSR KO) develop more tumours than control mice (INSR flox).

As seen in FIG. 1, the mice with intestinal specific inactivation of the insulin receptor (INSR KO) loose more weight during the DSS treatment and their recovery progresses more slowly as determined by the weight curves, compared to the wild type mice (INSR Flox). Importantly, in the AOM+DSS model the weight loss is a measure of the severity of the inflammation. In addition, the INSR KO mice develop twice as many tumours as the INSR floxed control mice (FIG. 2).

Results: These results indicate that a functioning insulin signalling is important for healing of inflamed colonic mucosa and for minimizing the occurrence of tumours in mice suffering from colitis (AOM+DSS treated mice).

Example 2. Rectal Insulin Administration Promotes Remission and Inhibits Tumour Development The discovery that inactivated insulin signalling in the intestine augments inflammation and stimulates development of inflammation induced tumours, prompted us to the invention that insulin might be used to treat colitis. This was investigated in an intervention study. Thus, wild type mice were set up in the AOM+DSS regime and divided into two groups. One group of mice was treated with rectal administration of insulin while the control group was treated with vehicle (phosphate buffered saline; PBS).

Figure 3:
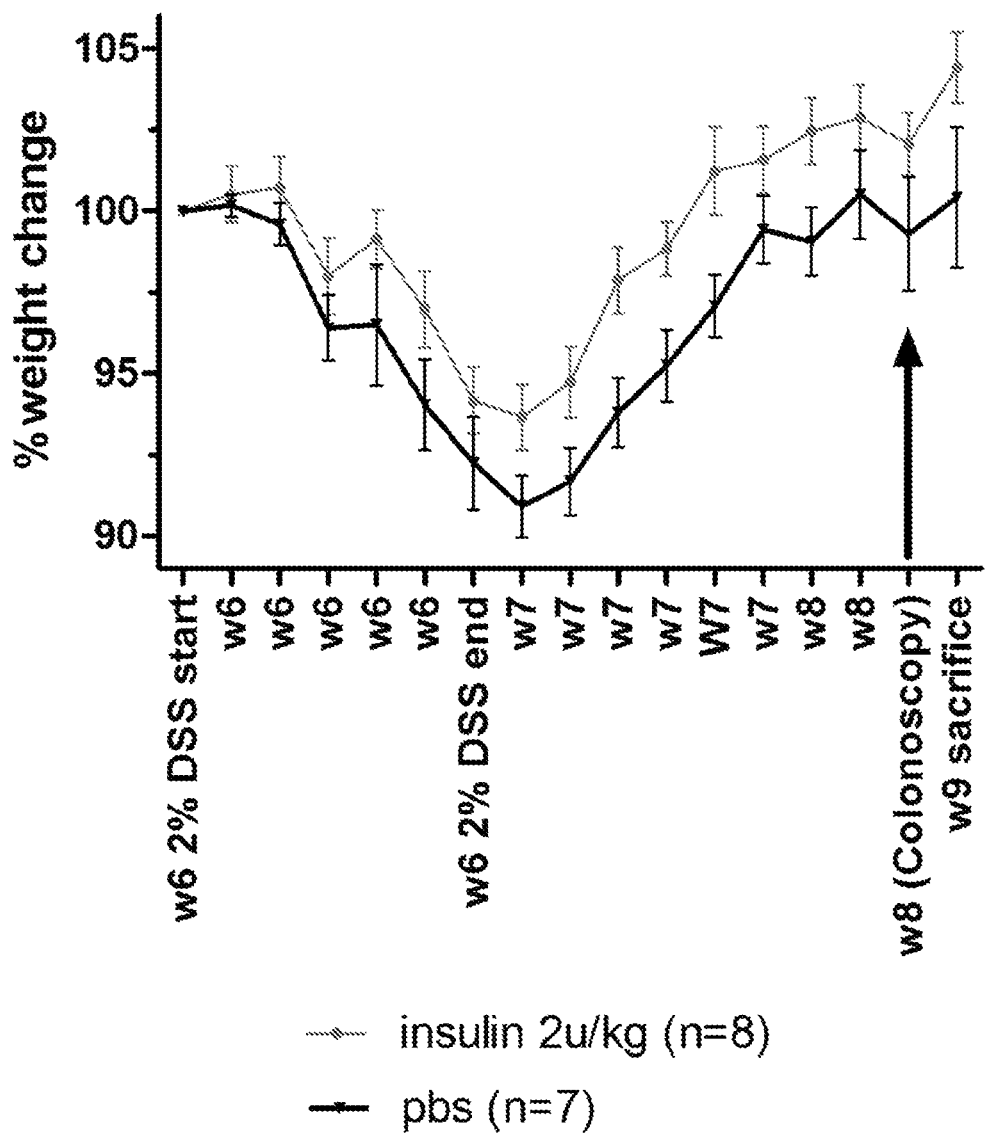
FIG. 3. Rectal Insulin treatment inhibits DSS induced colitis. Mice with DSS induced colitis were treated daily with rectal administered recombinant human insulin (2 units/kg) and re-gained weight.

The results show a significant difference (t-test, $p<0.05$) in the weight loss from DSS start (day 1) to beginning of remission (day 8—first w7 on FIG. 3). The weight losses were: 1.68 g (2.26; 1.09) in the insulin treated group and 2.56 g (3.19; 1.92) in the PBS group.

Figure 4:
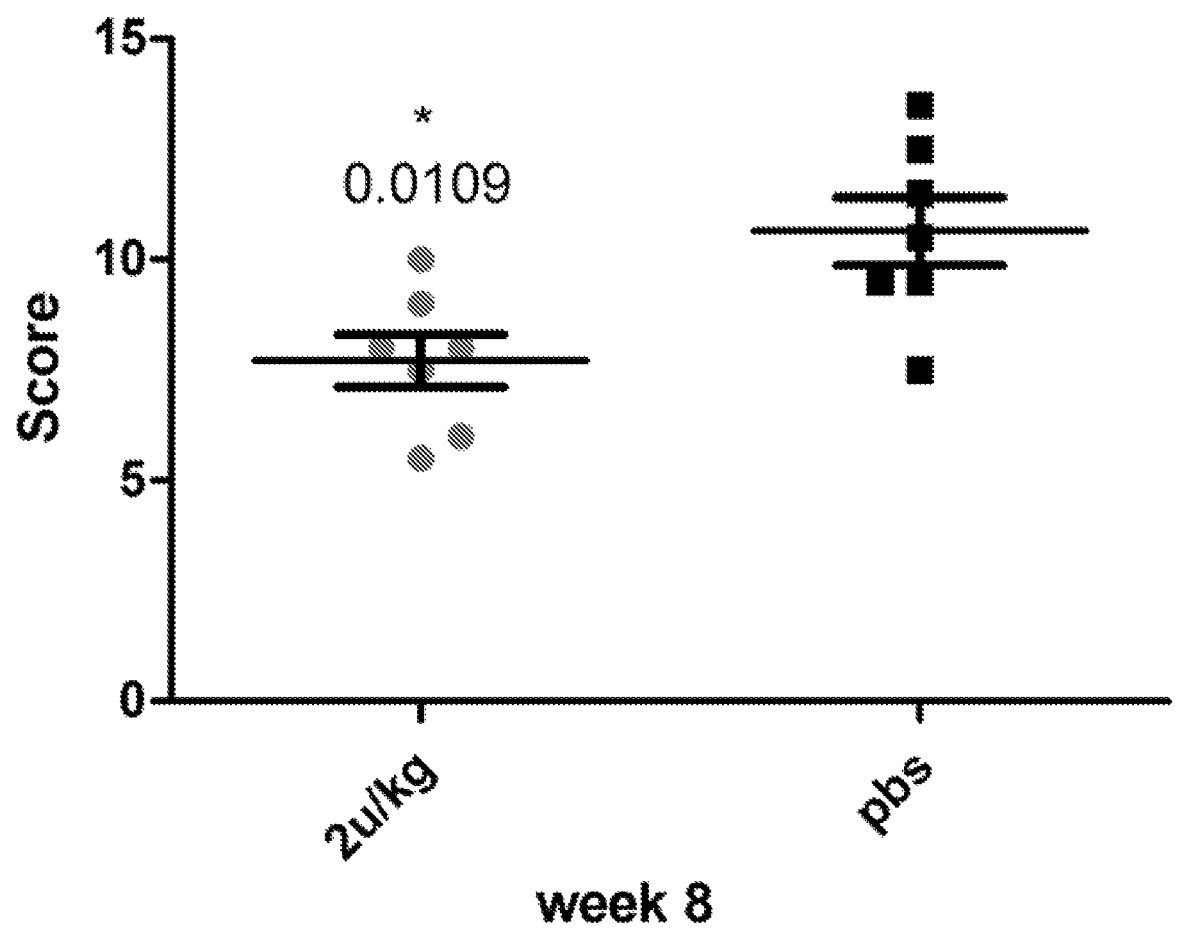
FIG. 4. Rectal insulin treatment improves inflammation score in the late remission phase of DSS induced colitis as determined by endoscopic (colonoscopic) inspection of the inflamed colon.

Anaesthetized mice were also subjected to colonoscopy in the late remission phase (arrow on FIG. 3) and the recorded videos of the endoscopy scored in a blinded fashion. The results (FIG. 4) show that the insulin treated mice has a significant lower (and better) inflammation score thus directly demonstrating that insulin affects the inflammation.

Blood per rectum is one sign of colitis and during the insulin treatment all mice receiving only PBS showed signs of rectal bleeding, whereas this was only observed in two insulin treated mice. This finding complements the results from the weight curves and also directly demonstrates that insulin treatment reduces the inflammation significantly ($p<0.05$) based on the rectal bleeding pattern observed. Moreover there was a significant reduction in the number of tumours with a size greater than 2 mm in the insulin treated group (0 mice had tumours >2 mm in the insulin group versus 1.3>2 mm tumours per mouse in the PBS group ($p<0.05$)).

The insulin treatment regime was as follows: Each day during DSS treatment and the following first 4 days during remission (no DSS treatment) the mice were anaesthetized with isoflurane and 600 μl PBS or PBS+0.06 units human insulin was injected intra rectally. For the injection, a syringe fitted with a flexible silicone feeding needle (for rodents) was used. The mice were placed on their back with the lower end elevated for 10 minutes while still in isoflurane anaesthesia. After recovery from anaesthesia the mice were returned to their cages. The mice were weighed daily and signs of rectal bleeding scored.

Please note that general anaesthesia prior to intra rectal administration of insulin is not a part of the invention. Anaesthesia is only required in order for the mice to tolerate the intra rectal administration. Rectal administration of pharmaceuticals in humans, however, is a well-known route of administration. It is easy to apply and well tolerated by the patients also without any kind of analgesia or anaesthesia.

Figure 5:
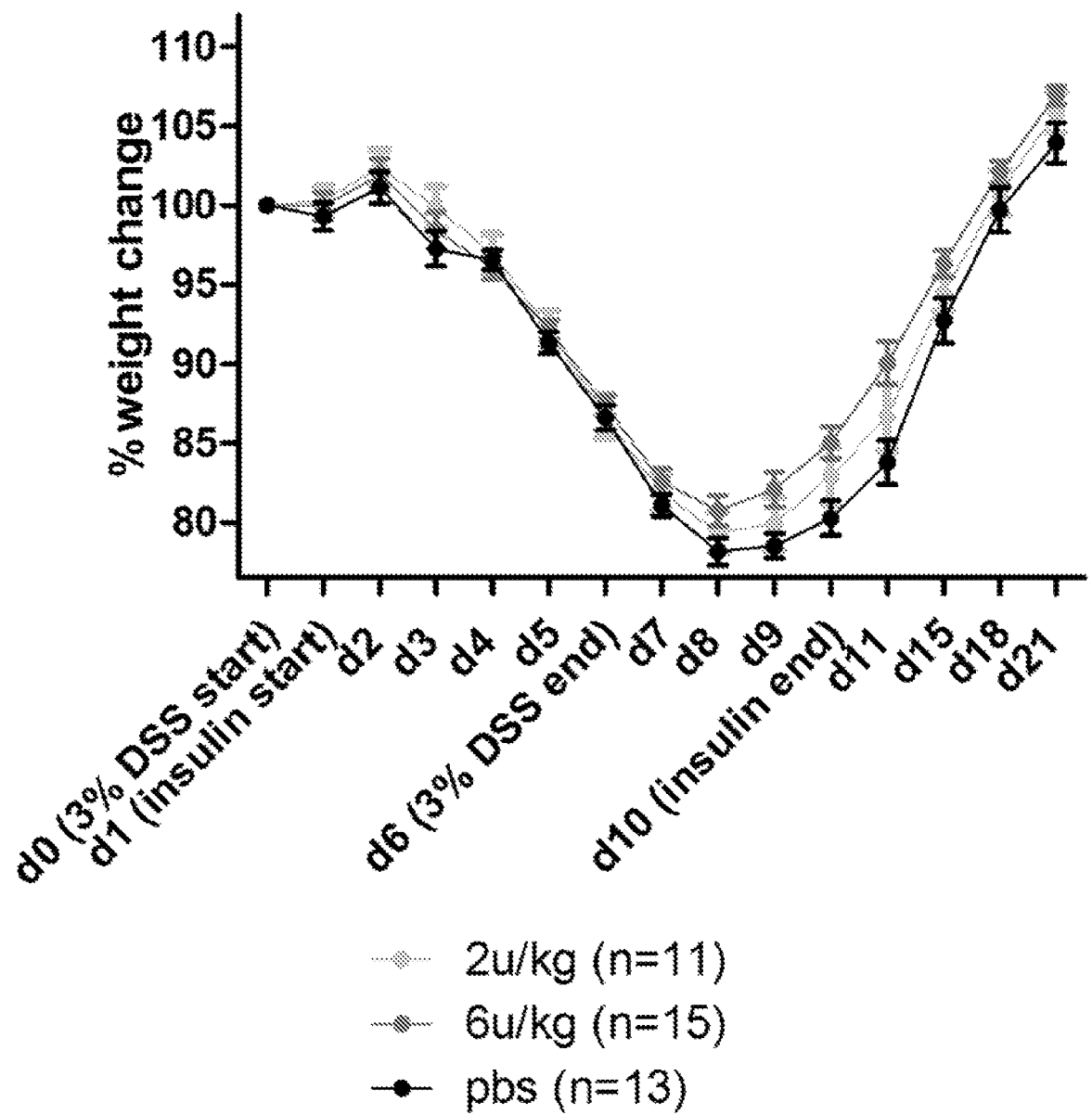
FIG. 5. Dose-response effect of rectal insulin treatment in mice with DSS induced colitis.
Figure 6:
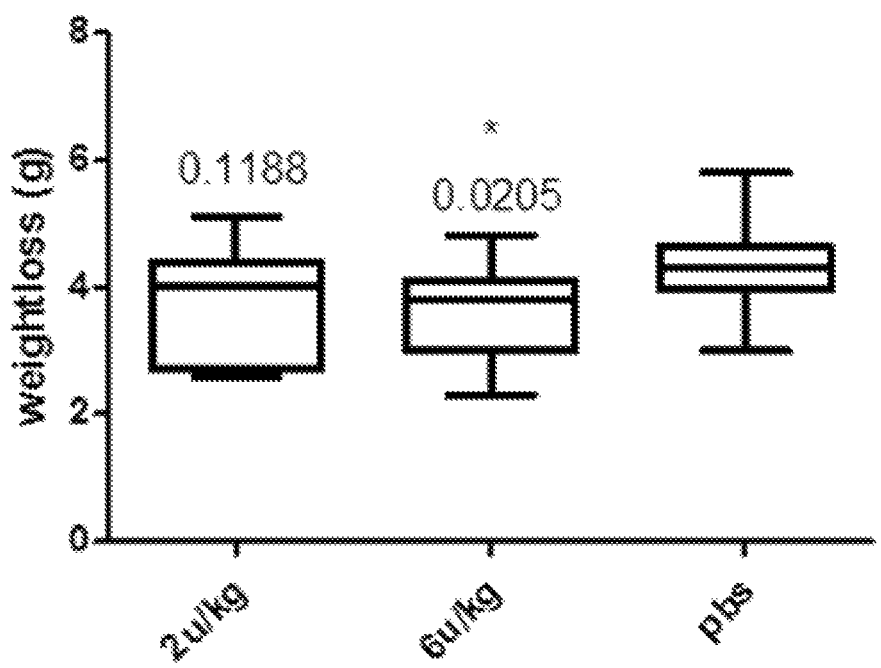
FIG. 6. Dose dependent protection of insulin treatment against inflammation-induced weight loss.

FIG. 5 shows the results of a separate AOM+DSS+rectal insulin experiment designed to investigate a dose-response effect of rectal insulin treatment. In this experiment 3% DSS was used as opposed to 2% DSS in the previous experiment (FIG. 3). During induction of inflammation there is a significant (FIG. 6, t-test, $p<0.05$) effect of the administration of 6 u/kg insulin whereas there is no effect of only 2 u/kg administration. Specifically the weight loss (weight at the end of DSS treatment–the weight at the beginning of the DSS treatment) is 16% less in the 6 u/kg insulin group compared to the PBS group (4.3 g in the PBS group versus 3.6 g in the 6 u/kg insulin group; see FIG. 5.

Figure 7:
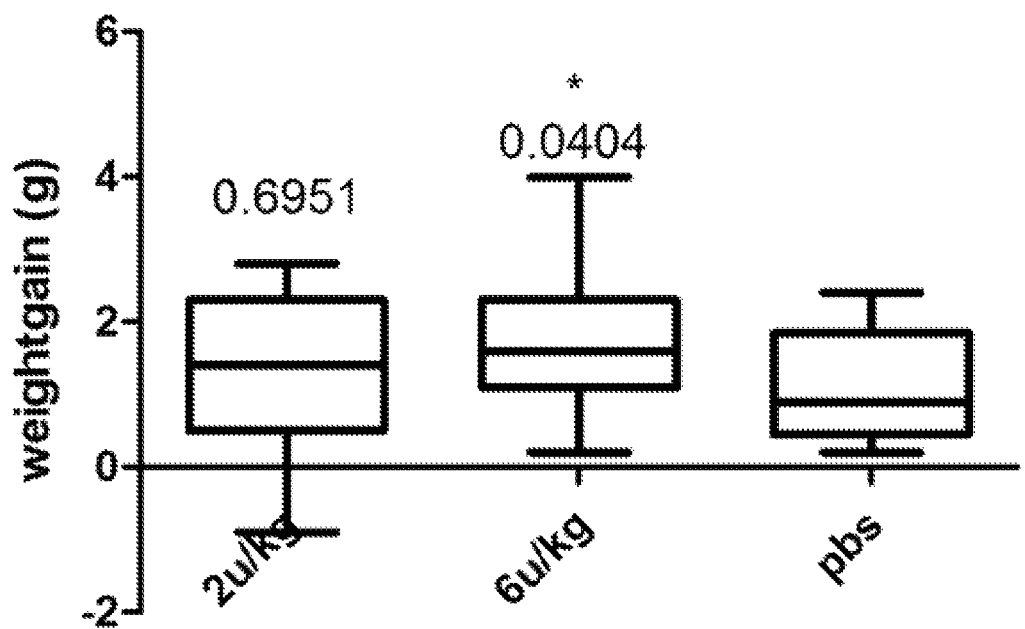
FIG. 7. Dose dependent remission phase weight gain of insulin treatment.

Concerning the remission phase following the end of DSS treatment (FIG. 5, day 6) there is a dose-dependent increase in weight from day 8 to day 11 following insulin treatment (FIG. 7).

With respect to rectal bleeding in this experiment the results were:

TABLE 1

Rectal bleeding in untreated and insulin-treated mice.

|  | Bleeding | No bleeding |
| --- | --- | --- |
| PBS group | 9 | 4 |
| 2 u/kg insulin | 3 | 8 |
| 6 u/kg Insulin* | 3 | 12 |

Thus there is a significant difference (*$p<0.05$, Fischer's exact test) between the 6 u/kg group and the PBS group. Again the rectal bleeding is a parameter for the degree of colorectal inflammation and the results therefore supports the notion of a dose dependent inhibition of inflammation by rectal insulin administration.

Figure 8:
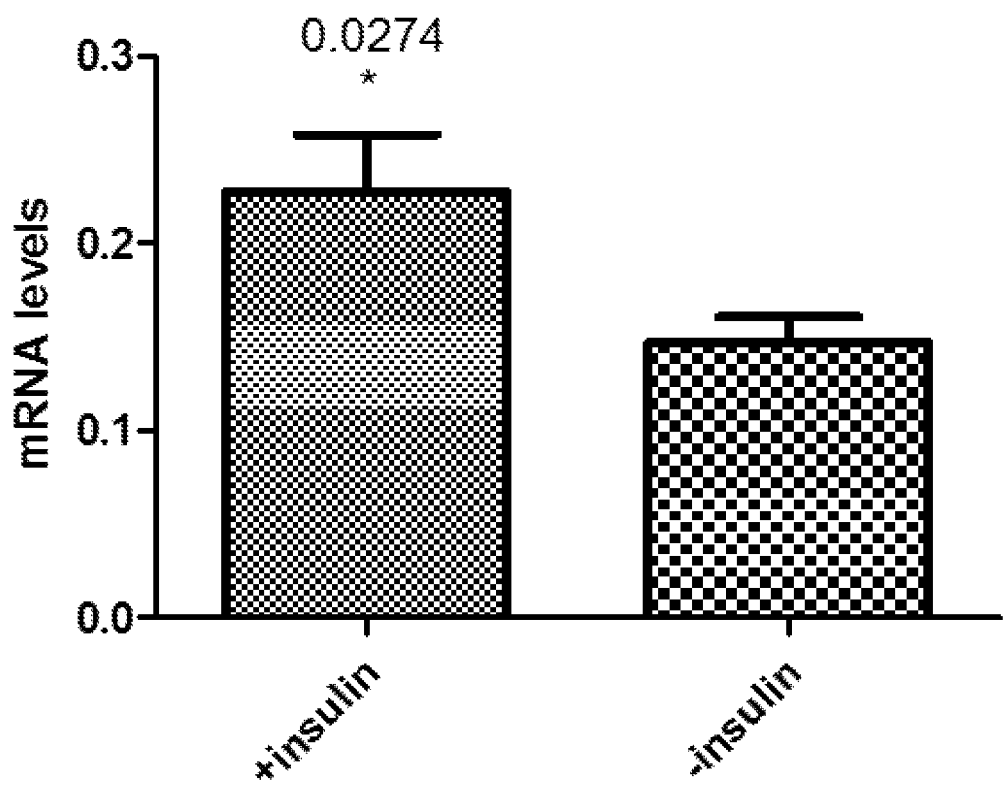
FIG. 8. Effect of insulin stimulation on insulin receptor mRNA expression on cultured colonic crypts.

To investigate the effect of insulin on isolated colonic epithelial cells, colonic crypts were cultured as organoids with and without the addition of insulin to the medium. FIG. 8 shows that the concentration of insulin receptor mRNA is increased almost two-fold by insulin treatment. Several mechanisms are possible. First it is possible that insulin induces differentiation of the epithelial cells and that this process increases insulin expression. Alternatively the insulin receptor may directly stimulate its own mRNA expression by yet undescribed mechanisms. The finding is important because the positive feedback loop is expected to prolong the duration of the insulin effect on the colonic mucosa.

Cyclooxygenase 2 (COX2/PTGS2) catalyzes the first step in the synthesis of the inflammatory mediators, the prostaglandins, from arachidonic acid. The expression of COX2 is increased in the colonic epithelial cells from patients with active colonic CD and UC and is therefore a biomarker for colonic inflammation in IBD.

Figure 10:
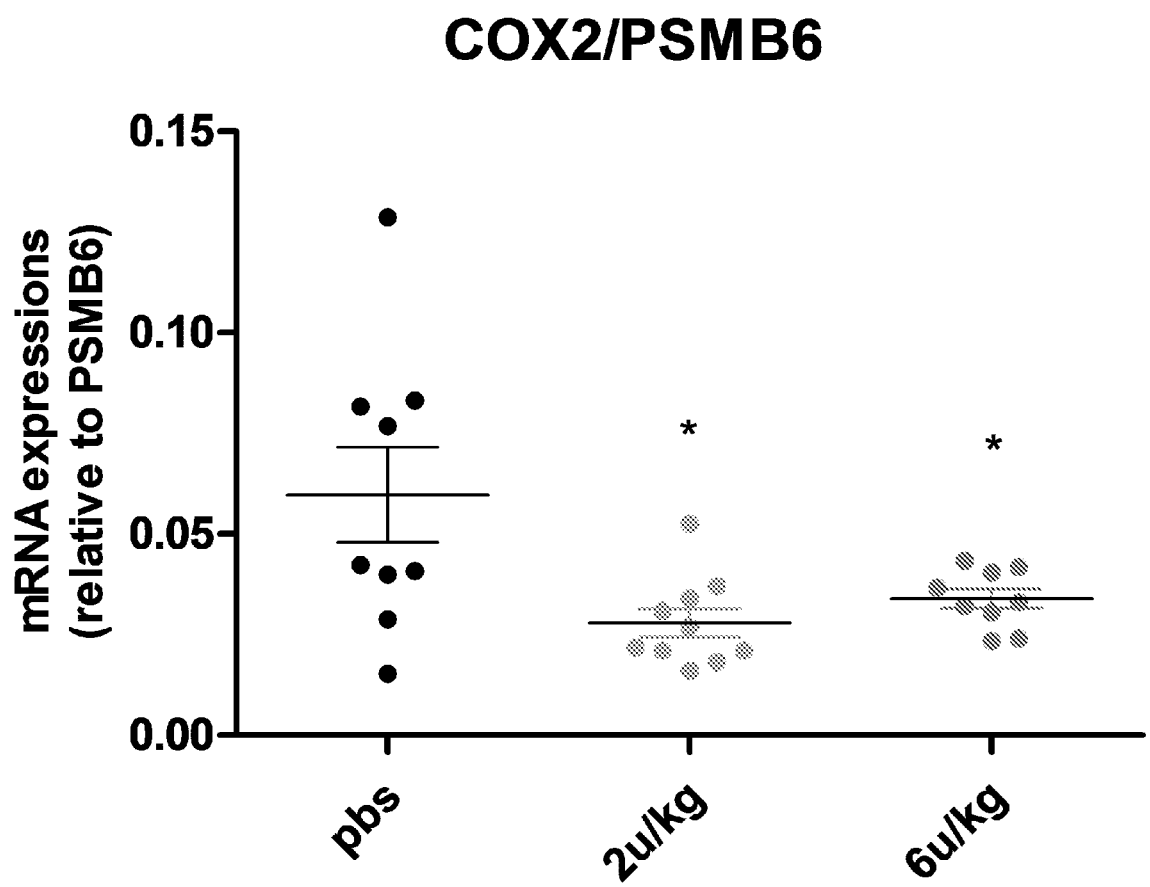
FIG. 10. Expression of COX2 in the colonic epithelial cells from patients with active colonic CD and UC.

FIG. 10 shows that the expression of COX2 mRNA in the colons of mice with AOM+DSS induced inflammation decreases when rectal insulin is administered. In particular, doses of either 2 u/kg or 6 u/kg were both able to significantly reduce the mRNA expression for COX2.

Results: These data indicate that rectal administration of insulin to AOM+DSS treated mice results in: reduced rectal bleeding, reduced weight loss, reduced inflammation (as seen from endoscopic and histological studies as well as from the decreased expression of the inflammatory mediator COX2) and reduced occurrence of colorectal tumours in comparison to AOM+DSS treated mice not treated with rectal insulin.

Example 3. Gene Expression in INSR+/+ and INSR−/−

To get some information about the effects of insulin signalling in colonic epithelial cells a DNA-microarray experiment was conducted using RNA extracted from inflamed colons from INSR+/+mice and INSR−/−mice. The data was analysed by a bioinformatics approach (pcaGoPromoter analysis) previously used by us to analyse genome-wide gene expression data from patients with IBD and using software developed by us. The principle behind the analysis is a principal component analysis of the gene expression data with the addition of a functional annotation of the principal component axes using statistical overrepresentation analysis. Thus in the case where a group of samples are drawn from cells undergoing mitosis and compared by pcaGopromoter analysis with another group of samples drawn from resting cells then the difference in multivariate gene expression will be reflected in the annotation analysis. Thus typically samples from cycling cells will be plotted along a PC axis annotated with terms such as "mitotic cell cycle", "cell cycle" and "M-phase". The results of the pcaGopromoter analysis of the samples from INSR+/+ and INSR−/−mice are shown in FIG. 9.

First it is seen that there is not a clear separation of the INSR+/+ and INSR−/−samples along any of the first two PC axes. Thus the overall difference in multivariate gene expression in the inflamed colons from INSR+/+mice and INSR−/−mice are small. However, in a model with the first 3 PC axes there is a significant difference in the multivariate gene expression between the INSR+/+ and INSR−/−samples (Hotelling T2 test, $p<0.05$).

Figure 9:
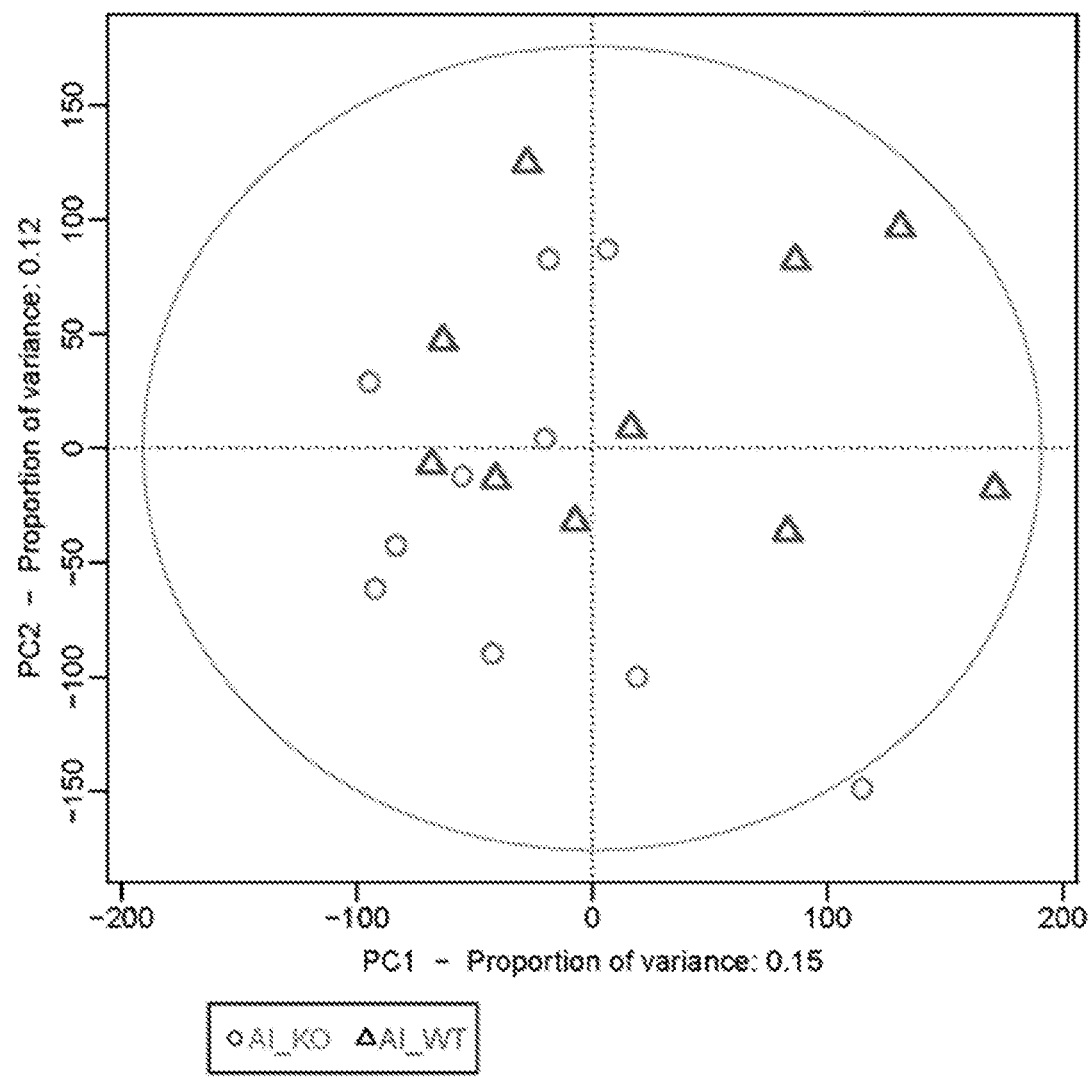
FIG. 9. DNA-microarray and pcaGOpromoter analyses of inflamed colonic samples from INSR−/−mice and INSR+/+ mice.

In FIG. 9 it can be seen that the INSR−/−samples are plotted mainly towards negative values on the first PC axis whereas the INSR+/+samples are evenly distributed between positive and negative values on the first PC axis. The negative direction of the first PC axis is annotated with the terms: "immune system process", "cell activation", "regulation of immune system process", "positive regulation of immune system process", "immune response". In contrast, the positive direction of the first PC is annotated with the terms "cation transmembrane transport", "ion transport", "cation transport", "ion transmembrane transport" and "transmembrane transport".

Thus from the bioinformatics analysis of the DNA microarray data it can be concluded that the samples from inflamed colons of INSR−/−mice are marginally more inflamed (at the molecular level) compared to the INSR+/+ samples. Moreover there is no evidence for more cell cycle activity in the colonic samples from wild type INSR+/+mice compared to samples from the INSR−/−knock out mice, indicating that the insulin signalling does not affect cell cycle in colonic epithelial cells.

Instead there is some evidence that the wild type samples have higher expression of genes involved in transmembrane ion transport.

Results: These results indicate that the mechanism behind insulin's healing effect on the AOM+DSS treated mice is more likely to involve improved epithelial ion transport rather than increased epithelial cell proliferation.

Example 4. Systemic Glucose Levels

Figure 11:
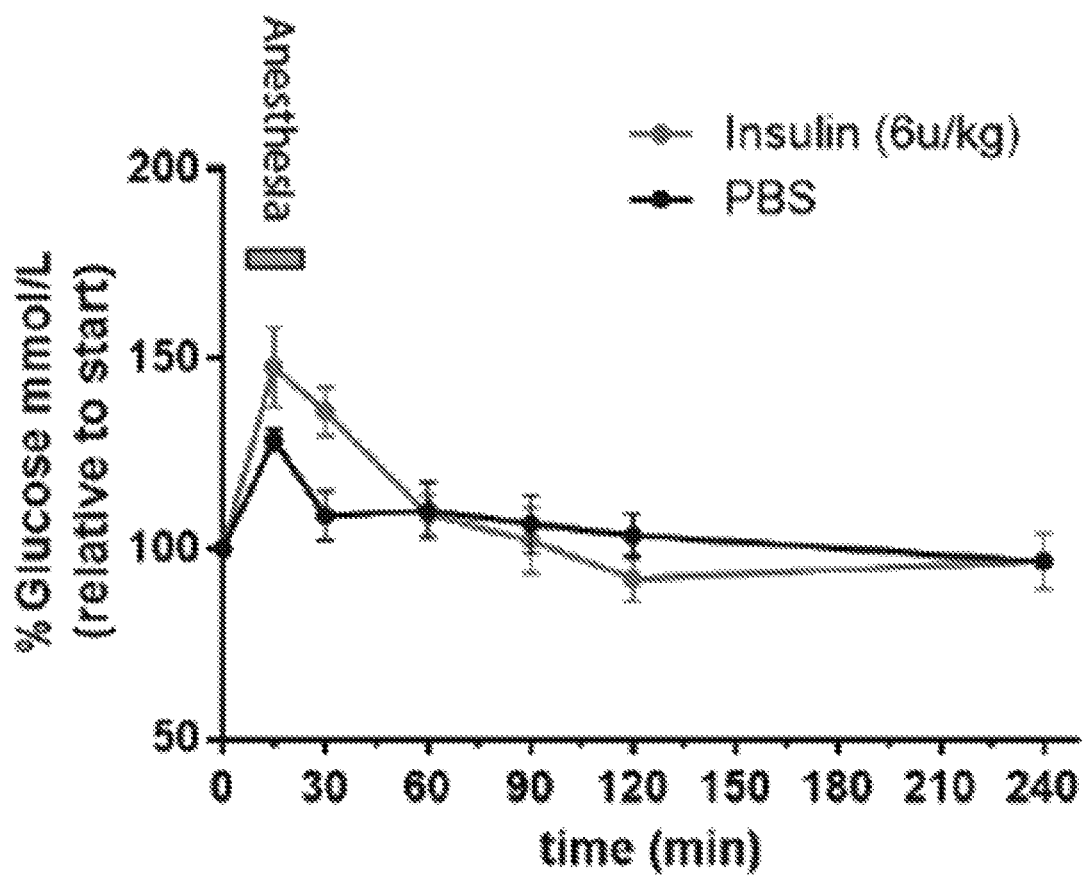
FIG. 11. Blood glucose concentration after rectal insulin or PBS instillation.

C57BL6 mice were treated with 3% DSS in their drinking water. At the peak of inflammation, the mice were treated with rectal insulin and the blood glucose concentration measured at 0, 15, 30, 60, 90, 120 and 240 minutes. Anaesthesia was induced after the first measurement was taken at time point zero. Anaesthesia was complete at time point 15 minutes and rectal insulin instillation or PBS control instillation also begun at time point 15 minutes. Anaesthesia resulted in a drop in the basic metabolic rate in the mice leading to a transient rise in blood glucose concentration in both control mice and in mice treated with insulin rectally. The mice had completely recovered from anaesthesia at time point 30 minutes. No significant difference was observed between PBS treated control mice and the mice treated with insulin rectally. Moreover the blood glucose concentration remained close to the initial level observed (time point zero) for each group except for the rise observed in both groups due to anaesthesia. These results are shown in FIG. 11.

Results: Rectal insulin does not have any effect on the systemic blood glucose concentration in the treated mice. Accordingly, the systemic uptake of insulin following rectal instillation of insulin to the lumen of the colon and rectum is negligible. Thus, the therapeutic effect of rectally administered insulin is a topical effect and it is observed directly on the epithelial cells of the lumen of the colon and rectum.

Example 5. Car3 Expression

From the microarray experiment described in Example 3 it could be seen that Carbonic anhydrase 3 (Car3) mRNA expression was significantly increased in INSR Flox mice during inflammation. On the contrary, in the INSR KO mice with inactivated insulin receptor in the intestinal epithelial cells the expression of Car3 was not increased by inflammation. Therefore it was investigated whether Car3 is a target for intestinal insulin signalling. The methodology described in Example 2 was followed.

Car3 encodes a cytosolic carbonic anhydrase and in the colonic epithelial cells carbonic anhydrases is involved in the electroneutral NaCl transport across the epithelium. Car3 also has a role as a scavenger of reactive oxygen species (ROS) (Raisanen et al. 1999).

Figure 12:
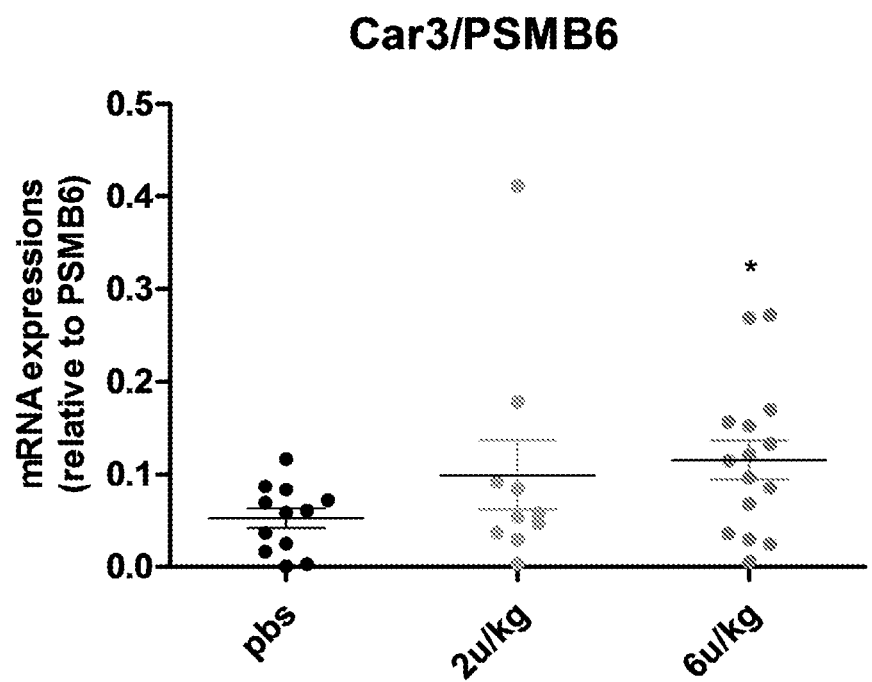
FIG. 12. Car3 mRNA expression in colons of mice treated with PBS, 2 u/kg or 6 u/kg rectal insulin during intestinal inflammation (AOM+DSS induced).

It was found that the expression of Car3 mRNA was significantly increased during intestinal inflammation (AOM+DSS induced) in the colon of mice treated with 6 u/kg insulin but not in mice treated with PBS or only 2 u/kg insulin as shown in FIG. 12.

Results: These results indicate that the mechanism behind insulin's healing effect on the AOM+DSS treated mice is more likely to involve improved epithelial ion transport and protection of the cells from the harm full effects of ROS released from inflammatory cells rather than increased epithelial cell proliferation.

Example 6. Proliferation of Colonic Epithelial Cells

Sections of mouse colons from INSR KO mice and INSR Flox mice were stained with an antibody against the proliferation marker Ki67. Thereafter, sections of inflamed (DSS induced) colons obtained from C57BL6 mice treated with either PBS, 2 u or 6 units/kg insulin were also stained with an antibody directed against the Ki67 proliferation marker and the number of KI67 positive cells per crypt counted.

Figure 13:
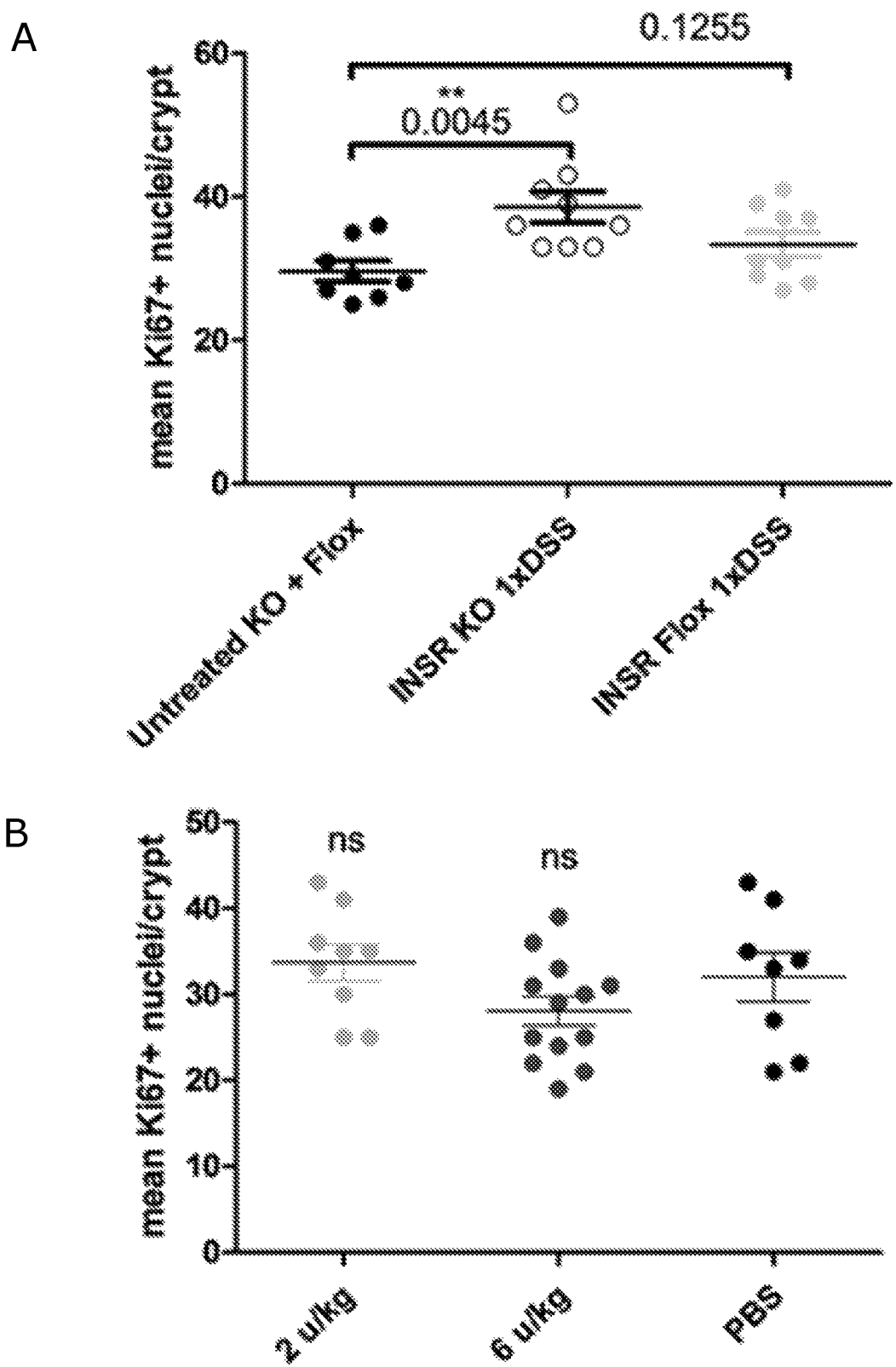
FIG. 13. Number of Ki67 positive crypt cells in (A) mouse colons from INSR KO mice and INSR Flox mice and (B) C57BL6 mice treated with either PBS, 2 u or 6 units/kg insulin.

A significant increase in Ki67 positive crypt cells was only found for the mice lacking the insulin receptor in the epithelial cells (INSR KO) as shown in FIG. 13A. No significant difference in the staining patterns of sections of colon obtained from mice treated with PBS, 2 u or 6 units/kg insulin was found as shown in FIG. 13B.

Results: The results indicate that rectal insulin therapy does not induce proliferation of the colonic epithelial cells.

REFERENCES

Terzic J, Grivennikov S, Karin E and Karin M, 2010. Inflammation and Colon Cancer. Gastroenterology 138: 2101-2114.
Wehkamp J, Götz M, Herrlinger K, Steurer W and Stange E F, 2016. Inflammatory Bowel Disease, Crohn's disease and ulcerative colitis. Dtsch Arztebl Int. 113(5): 72-82.
Räisänen et al. 1999, Carbonic anhydrase III protects cells from hydrogen peroxide-induced apoptosis, FASEB Journal 13(3):513-22
Katsuma M, Watanabe S, Takemura S, Sako K, Sawada T, Masuda Y, Nakamura K, Fukui M, Connor A L, Wilding I R. (2004). Scintigraphic evaluation of a novel colon-targeted delivery system (CODES) in healthy volunteers. J Pharm Sci May; 93(5):1287-99
Woods S P and Constandinou T G (2013) Wireless Capsule Endoscope for Targeted Drug Delivery: Mechanics and Design Considerations, IEEE TRANSACTIONS ON BIOMEDICAL ENGINEERING, VOL. 60, NO. 4

The invention claimed is:

1. A method for treatment of a subject that has an inflammatory bowel disease or inflammation-induced colorectal tumour or cancer, the method comprising administering locally to the large intestine a composition comprising a therapeutically effective amount of insulin or a pharmaceutically acceptable salt thereof, wherein the composition does not affect systemic blood glucose levels.

2. The method according to claim 1, wherein the subject has an inflammatory bowel disease selected from the group consisting of ulcerative colitis, diversion colitis, Behçet's disease, indeterminate colitis, left sided colitis, microscopic colitis, Crohn's disease, noninfective colitis and pouchitis.

3. The method according to claim 1, wherein the composition comprises between 0.35 µg and 35 g of insulin.

4. The method according to claim 1, wherein the composition comprises between 0.01 and 10 IU/ml of insulin.

5. The method according to claim 1, wherein the total dose of insulin per day is between 0.01 IU and 1000 IU.

6. The method according to claim 1, wherein the composition is administered to the subject over a period of at least 3 weeks.

7. The method according to claim 1, wherein the composition is administered to the subject during the remission phase of the inflammatory bowel disease or inflammation-induced colorectal tumour or cancer for a period between 3 weeks and 3 months.

8. The method according to claim 1, wherein the composition is locally administered to the large intestine in the form of a rectal foam, a gel, an enema, an aerosol, an ointment, a cream, a gastric lavage, a suppository, a rectal lavage using a catheter, a mechanical insulin release device orally ingested or a pharmaceutical colonic release system, or via a percutaneous catheter, via an intraintestinal catheter, endoscopically, or via a mechanical intraluminal device.

9. The method according to claim 1, wherein the composition is administered to the subject during the acute phase of the inflammatory bowel disease or inflammation-induced colorectal tumour or cancer.

10. The method according to claim 1, wherein the composition is administered to the subject during relapse of the inflammatory bowel disease or inflammation-induced colorectal tumour or cancer.

11. The method according to claim 1, wherein the composition is administered to the subject during the remission phase of the inflammatory bowel disease or inflammation-induced colorectal tumour or cancer.

12. The method according to claim 1, wherein the inflammatory bowel disease is mild to moderate ulcerative colitis.

13. The method according to claim 1, wherein the inflammatory bowel disease is mild to moderate ulcerative colitis, and wherein the composition is administered to the subject during the acute phase or during relapse of the disease.

14. The method according to claim 1, wherein the composition is capable of reducing inflammation of epithelial cells of the colon.

15. The method according to claim 1, wherein the composition is capable of reducing expression of COX2 mRNA.

16. The method according to claim 1, wherein the composition is capable of improving epithelial ion transport in the large intestine.

17. The method according to claim 1, wherein the composition does not cause cell proliferation in the small intestine.

18. The method according to claim 1, wherein the composition further comprises a protease inhibitor or an antibiotic.

19. The method according to claim 1, wherein the composition has low or no systemic effects.

20. A method of reducing weight loss in a subject that has an inflammatory bowel disease or inflammation-induced colorectal tumour or cancer, the method comprising administering locally to the large intestine a composition comprising a therapeutically effective amount of insulin or a pharmaceutically acceptable salt thereof, wherein the composition does not affect systemic blood glucose levels.

21. A method of healing colonic mucosa in a subject that has an inflammatory bowel disease or inflammation-induced colorectal tumour or cancer, the method comprising administering locally to the large intestine a composition comprising a therapeutically effective amount of insulin or a pharmaceutically acceptable salt thereof, wherein the composition does not affect systemic blood glucose levels.

* * * * *